(12) United States Patent
Karp et al.

(10) Patent No.: US 9,962,339 B2
(45) Date of Patent: May 8, 2018

(54) STABILIZED ASSEMBLED NANOSTRUCTURES FOR DELIVERY OF ENCAPSULATED AGENTS

(71) Applicant: The Brigham and Women's Hospital, Inc., Boston, MA (US)

(72) Inventors: Jeffrey M. Karp, Cambridge, MA (US); Nitin Joshi, Cambridge, MA (US); Nikken Wiradharma, Cambridge, MA (US); Kai Vincent Slaughter, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days. days.

(21) Appl. No.: 15/288,816

(22) Filed: Oct. 7, 2016

(65) Prior Publication Data
US 2017/0100342 A1    Apr. 13, 2017

Related U.S. Application Data

(60) Provisional application No. 62/239,211, filed on Oct. 8, 2015.

(51) Int. Cl.
| | |
|---|---|
| *A61K 9/16* | (2006.01) |
| *A61K 9/51* | (2006.01) |
| *A61K 31/337* | (2006.01) |
| *A61K 49/00* | (2006.01) |
| *A61K 9/00* | (2006.01) |

(52) U.S. Cl.
CPC .......... *A61K 9/5123* (2013.01); *A61K 9/0019* (2013.01); *A61K 31/337* (2013.01); *A61K 49/0093* (2013.01)

(58) Field of Classification Search
CPC .......... A61K 9/16; A61K 9/14; A61K 9/1605; A61K 9/1629; A61K 9/1659; A61K 9/167
See application file for complete search history.

(56) References Cited

U.S. PATENT DOCUMENTS

| | | | |
|---|---|---|---|
| 5,603,959 | A | 2/1997 | Horrobin |
| 6,471,970 | B1 | 10/2002 | Fanara et al. |
| 7,749,485 | B2 | 7/2010 | Tournier |
| 2005/0084470 | A1 | 4/2005 | Husain |
| 2006/0276676 | A1 | 12/2006 | van Bommel |
| 2008/0004398 | A1 | 1/2008 | Durriru |
| 2008/0038316 | A1 | 2/2008 | Wong |
| 2009/0110735 | A1 | 4/2009 | Maggio |
| 2009/0169498 | A1 | 7/2009 | de Jong |
| 2010/0129451 | A1 | 5/2010 | John |
| 2013/0273140 | A1 | 10/2013 | Maggio |
| 2013/0280334 | A1* | 10/2013 | Karp ..................... A61K 9/0019 424/490 |
| 2013/0309286 | A1 | 11/2013 | Engstad |
| 2014/0302144 | A1 | 10/2014 | Koutsopoulos |
| 2015/0202586 | A1* | 7/2015 | Imoto ..................... A61K 8/64 516/103 |

FOREIGN PATENT DOCUMENTS

| | | |
|---|---|---|
| EP | 1063007 | 12/2000 |
| EP | 0517211 | 9/2004 |
| EP | 2361640 | 8/2011 |
| FR | 2417494 | 9/1979 |
| WO | 9907416 | 2/1999 |
| WO | 2006008386 | 1/2006 |
| WO | WO 2006/008386 | 1/2006 |
| WO | 2010033726 | 3/2010 |
| WO | WO 2010/033726 | 3/2010 |
| WO | 2012040623 | 3/2012 |
| WO | 2014089472 | 6/2014 |

OTHER PUBLICATIONS

Bennett, et al., "Next-generation hydrogel films as tissue sealants and adhesion barriers," *Cardiac Surgery*, 18:494-9 (2003).
Bhattacharya, et al., "In Molecular Gels," Kluwer Academic Publishers: The Netherlands (2004).
Bhuniya, et al., "(S)-(+)-Ibuprofen-Based Hydrogelators: An Approach Toward Anti-Inflammatory Drug Delivery," *Tetrahedron Lett.*, 47:7153-6 (2006).
Bong, et al., "Self-Assembling Organic Nanotubes," *Angew Chem. Int.*, 40:988-1011 (2001).
Bonte and Juliano, "Interactions of liposomes with serum proteins," *Chem Phys Lipids*, 40:359-72 (1986).
Boutaud, et al., "Determinants of the Cellular Specificity of Acetaminophen as an Inhibitor of Prostaglandin H(2) Synthases," *PNAS*, 99:7130-5 (2002).
Bryers, et al., "Biodegradtion of Poly(anhydride-esters) into Non-Steroidal Anti-Inflammatory Drugs and Their Effect on Pseudomonas aeruginosa Biofilms in Vitro and on the Foreign-Body Response in Vivo," *Biomaterials*, 27:5039-48 (2006).
Burns, et al., "Physical characterization and lipase susceptibility of short chain lecithin/triglyceride mixed micelles", *J Biol Chem.*, 256(6):2716-22 (1981).
Casuso, et al., "Converting drugs into gelators: supramolecular hydrogels from N-acetyl-L-cysteine and coinage-metal salts", *Org Biomol Chem.*, 8:5455-8 (2010) Abstract Only.
Chourasia, et al., "Pharmaceutical Approaches to Colon-Targeted Drug Delivery Systems," *Pharm. Pharmaceut. Sci.*, 6:22-66 (2003).
Erdmann, et al., "Degradable Poly(anhydridie ester) Implants: Effects of Localized Salicylic Acid Release on Bone," *Biomaterials*, 21:2507-12 (2000).

(Continued)

*Primary Examiner* — Micah Paul Young
(74) *Attorney, Agent, or Firm* — Pabst Patent Group LLP

(57) ABSTRACT

A non-covalently assembled hydrogel or organo-gel composition with serum stability is described. Low molecular weight (<2,500 Da), generally regarded as safe (GRAS), materials assemble in the presence of a stabilizing agent at an appropriate molar percentage, forming hydrogel or organo-gel with nanostructures that resist disassembly or destabilization in serum for an extended period of time. The composition is used to deliver one or more therapeutic, prophylactic, or diagnostic agents, allowing for controlled release in response to biological stimuli such as enzymes and a greatly improved dosing efficacy.

30 Claims, 10 Drawing Sheets

(56) References Cited

OTHER PUBLICATIONS

Estroff, et al., "Effective Gelation of Water Using a Series of Bis-urea Dicarboxylic Acids," *Angew. Chem. Int. Ed.*, 39:3447-3450 (2000).
Fischel-Ghodsian, et al., "Enzymatically Controlled Drug Delivery," *PNAS*, 85:2403-6 (1988).
Friggeri, et al., "Entrapment and release of quinoline derivatives using a hydrogel of a low molecular weight gelator", *Controlled Release*, 97:241-8 (2004).
Goopinath, et al., "Ascorbyl palmitate vesicles (aspasomes): formation, characterization and applications", *Intl J Pharma.*, 271(1-2):95-113 (2004).
Gong, et al., "Synthesis of hydrogels with extremely low surface friction", *J Am. Chem. Soc.*, 123:,5582-3 (2001).
Gupta, et al., "Hydrogels from controlled release to pH-responsive drug delivery", *Drug Discovery Today*, 7:569-79 (2002).
Han, et al., "Catalytic ester-amide exchange using group (iv) metal alkoxide-activator complexes", *JACS*, 127:10039-44 (2005).
Hans, et al., "Synthesis and characterization ofmPEG-PLA prodrug micelles", *Biomacromolecules*, 6:2708-17 (2005).
Harten, et al., "Salicylic acid-derived poly(anhydride-esters) inhibit bone resorption and formation in vivo", *Biomed. Mater. Res-A*, 72A:354-62 (2005).
Hoare, et al., "Hydrogels in drug delivery: Progress and challenges", *Polymer*, 49:1993-2007 (2008).
Huang, et al., "On the importance and mechanisms of burst release in matrix-controlled drug delivery svstems", *Controlled Release*, 73:121-36 (2001).
Jen, et al., "Review. Hydrogels for cell immobilization", *Biotechnol. Bioeng.*, 50:357-64 (1996).
John, et al., "Unsaturation effect on gelation behavior of aryl glycolipids", *Langmuir*, 20:2060-5 (2004)b.
John, et al., "Biorefinery. a design tool for molecular gelators," *Langmuir.*, 26:17843-51 (2010).
John, et al., "Nanotube Formation from Renewable Resources via Coiled Nanofibers", *AdV. Mater.*,13:715-8 (2001).
John, et al., "Enzymatically Derived Sugar-Containing Self-Assembled Organogels with Nanostructured Morphologies," *Angew Chem. Int. Ed.*, 45:4772-5, 2006b.
John, et al., "Morphological control of helical solid bilayers in high-axial-ratio nanostructures through binary self-assembly", *Chem. Eur. J.*, 8:5494-500 (2002).
John, et al., "Lipid-based nanotubes as functional architectures with embedded fluorescence and recognition capabilities", *J. Am. Chem. Soc.*, 126:15012-3 (2004).
Jovanovic, et al., "How curcumin works preferentially with water soluble antioxidants", *Chem. Soc.*, 123:3064-8 (2001).
Jung, et al., "Self-Assembly of a Sugar-Based Gelator in Water. Its Remarkable Diversity in Gelation Ability and Aggregate Structure," *Lanumuir*, 17:7229-32 (2001).
Kalgutkar, et al., "Ester and Amide Derivatives of the Nonsteriodal Antiinflammatory Drug, Indomethacin, as selective cvclooxvgenase-2 inhibitors," *J. Med. Chem.*, 43:2860-70 (2000).
Kamath, et al., "Biodegradable Hydrogels in Drug Delivery," *Adv. Drug Deliv. Rev.*, 11:59-84 (1993).
Kim, et al., "In vivo evaluation of polymeric micellar paclitaxel formulation. toxicity and efficacy", *Controlled Release*, 72:191-202 (2001).
Kiyonakam, et al., Semi-wet peptide/protein array using supramolecular hydrogel, *Nat. Mater.*, 3:58-64 (2004).
Kobayashi, et al., "Molecular design of "super" hydrogelators. understanding the gelation process of azobenzene-based sugar derivatives in water", *Org. Lett.* 4:1423-6 (2002).
Kumar, et al., "First snapshot of a nonpolymeric hydrogelator interacting with its getting solvents", *Chem. Commun.*, 4059-62 (2005).
Kumar, et al., "Prodrugs as self-assembled hydrogels: a new paradigm for biomaterials", *Biotech.*, 24:1-9 (2013).
Lee, et al., "Hydrogels for Tissue Engineering", *Chem. Rev.*, 101:1869-80 (2001).
Li, et al., "Molecular nanofibers of olsalazine form supramolecular hydrogels for reductive release of an anti-inflammatory agent", *JACS*, 132:17707-9 (2010).
Loos, et al., "Design and Application of Self-Assembled Low Molecular Weight Hydrogels," *Eur. J.of Organic Chem.*, 17:3615-31 (2005).
Lu, et al., "Photopolymerization of multilaminated poly(HEMA) hydrogels for controlled release", *J Controlled Release*, 57:291-300 (1999).
Luboradzki, et al., "An Attempt to Predict the Gelation Ability of Hydrogen-Bond-Based Gelators Utilizing a Glycoside Library," *Tetrahedron*, 56:9595-9 (2000).
Makarevic, et al., "Bis(amino acid) oxalyl amides as ambidextrous gelators of water and organic solvents. supramolecular gels with temperature dependent assembly/dissolution equilibrium", *Chem. Eur. J.*, 7:3328-41 (2001).
Mazumdar, et al., "Preparation and evaluation of ethambutol derivatives," *Indian J. Pharm. Sci.*, 47:179-80 (1985).
Menger, et al., "Anatomy of a Gel. Amino Acid Derivatives that Rigidify Water at Submillimolar Concentrations," *J. Am. Chem. Soc.*, 122:11679-91 (2000).
Miyata, et al., "Biomolecule-Sensitive hydrogels," *Adv. Drug Deliv. Rev.*, 54:79-98 (2002).
Molinier, et al., PFGSE-NMR study of the self-diffusion of sucrose fatty acid monoesters in water, *J Colloid Interface Sci.*, 286(1):360-8 (2005) Abstract Only.
Nicolaou, et al., "A Water-Soluble Prodrug of Taxol with Self-Assembling Properties," *Angew.Chem. Int. Ed.*, 33:1583-7 (1994).
Oda, et al., "Gemini Surfactants as New, Low Molecular Weight Gelators of Organic Solvents and Water," *Angew. Chem. Int. Ed.*, 37, 2689-91 (1998).
Palma, et al., "Evaluation of the surfactant properties of ascorbyl palmitate sodium salt", *EU J Pharma Sci.*, 16:37-43 (2002).
Peppas, et al., "Hydrogels in Biology and Medicine. From Molecular Principles to *Bionanotechnology*," *Adv. Mater.*, 18:1345-60 (2006).
Peppas, et al., "Hydrogels in pharmaceutical formulations," *Eur. J Pharm. Biopharm.*, 50:27-46 (2000).
Peppas, "Hydrogels and Drug Delivery," *Curr. Opin. Colloid Interface Sci.*, 2:531-7 (1997).
Persico, et al., "Effect of tolmetin glycine amide (McN-4366) a prodrug of tolmetin sodium on adjuvant arthritis in the rat", *J Pharma Exp Therap.*, 247(3):889-96 (1988).
Pietzyk, et al., "Degradation of phosphatidylcholine in liposomes containing carboplatin in dependence on composition and storage conditions", *Intl J Pharma.*, 196(2):215-8 (2000).
Poulsen, et al., "Effect of topical vehicle composition on the in vitro release of fluocinolone acetonide and its acetate ester", *J Pharma Sci.*, 57(6):928-33 (1968).
Qiu, et al., "Environment-sensitive hydrogels for drug dc/ivory,"*Adv. Drug Deliv. Rev.*, 53:321-39 (2001).
Rajabalaya, et al., "Studies on the effect of plasticizer on in vitro release and ex vivo permeation from Eudragit E 100 based", *J Excipients Food Chem.*, 1(2):1-12 (2010).
Rattie, et al., "Acetaminophen Prodrugs III. Hydrolysis of Carbonate and Carboxylic Acid Esters in Aqueous Buffers," *J. Pharm. Sci.*, 59:1738-41 (1970).
Robinson, et al., "Design, synthesis, and biological evaluation of angiogenesis inhibitors. Aromatic enone and dienone analogues of curcumin", *Biorg. Med. Chem. Lett.*, 13:115-7 (2003).
Rooseboom, et al., "Enzyme-catalyzed activation of anticancer prodrugs", *Pharmacol. Rev.*, 56:53-102 (2004).
Sinha et al., "Microbially triggered drug delivery to the colon", *Eur. J Pharm. Sci*, 18:3-18 (2003).
Sreenivasachary, et al., "Gelation-driven component selection in the generation of constitutional dynamic hydrogels based on guanine-quartet formation", PNAS, 102:5938-43 (2005).
Szuts, et al., "Study of thermos-sensitive gel-forming properties of sucrose stearates", *J Excipients Food Chem.*, 1(2):13-20 (2010).
Toth and Urtis, "Commonly used muscle relaxant therapies for acute low back pain: A review of carisoprodol cyclobenzaprine hydrochloride, and metaxalone", *Clin Therap.*, 26(9):1355-67 (2004).

(56) References Cited

OTHER PUBLICATIONS

Trouet, et al., "Extracellularly tumor-activated prodrugs for the selective chemotherapy of cancer application to doxorubicin and preliminary in vitro and in vivo studies", *Cancer Res.*, 61: 2843-6 (2001).
Troung, et al., "Self-assembled gels for biomedical applications", *Focus Rev.*, 6:30-42 (2011).
Ullrich, et al., "Sucrose ester nanodispersions: Microviscosity and viscoelastic properties", *Eu J Pharma Biopharma.*, 70:550-5 (2008).
Van Bommel, et al., "Two-stage enzyme medicated drug release from LMWG hydrogels", *Org Biomol Chem.*, 3:2917-20 (2005).
van der Linden, et al., "Stimulus-sensitive hydrogels and their applications in chemical (micro)analysis", *Analyst*, 128:325-31 (2003).
van Esch and Feringa,"New functional materials based on self-assembling organogels: From serendipity towards design", *Angew Chem Ltrs.*, 39(13):2263-6 (2000).
Vassilev, et al., "Enzymatic Synthesis of a Chiral Gelator with Remarkably Low Molecular Weight," *Chem. Commun.*, 1865-66 (1998).
Vemula, et al., "In Situ Synthesis of Gold Nanoparticles using Molecular Gels and Liquid Crystals from Vitamin-C Amphiphiles," *Chem. Mater.*, 19:138-40 (2007).
Vemula, et al., "Enzyme Catalysis. Tool to Make and Break Amygdalin Hydrogelators from Renewable Resources. A Delivery Model for Hydrophobic Drugs", *J. Am. Chem. Soc.*, 128: 8932-8 (2006).
Vemula, et al., "Smart Amphiphiles. Hydro/Organogelators for in Situ Reduction of Gold", *Chem.Commun.*, 2218-20 (2006b).
Vigroux, et al., "Cyclization-activated prodrugs: N-(substituted 2-hydroxyphenyl and 2-hydroxypropyl)carbamates based on ring-opened derivatives of active benzoxazolones and oxazolidinones as mutual prodrugs of acetaminophen", *J Med Chem.*, 38:3983-94 (1995).
Vohra, et al., "Nanolipid carrier-based thermoreversible gel for localized delivery of docetaxel to breast cancer", *Cancer Nanotech.*, 4(1-2):1-12 (2013).
Wang, et al., "Low Molecular Weight Organogelators for Water," *Chem. Commun.*, 310-311 (2003).
Wang, et al., "Hydrogels as separation agents, Responsive Gels. Volume Transitions II," *Advances in Polymer Science*, 67-79 (1993). Abstract Only.
Whitesides, et al., "Beyond molecules self-assembly of mesoscopic and macroscopic components", *PNAS*, 99:4769-74 (2002).
Xiog, et al., "Hydrophobic Interaction and Hydrogen Bonding Cooperatively Confer a Vancomycin Hydrogel a Potential Candidate for Biomaterials," *J. Am. Chem. Soc.*, 124:14846-7 (2002).
Yan, et al., "Enzymatic Production of sugar Fatty Acids Esters," PhD thesis, University of Stuttgard, (2001).
Yang, et al., "Small Molecular Hydrogels Based on a Class of Anti-Inflammatory Agents," *Chem. Commun.*, 208-209 (2004).
Yang, et al., "Enzymatic Hydrogelation of small Molecules", *Ace. Chem. Res.*, 41:315-26 (2008).
Yang, et al., "Enzymatic Formation of Supramolecular Hydrogels," *Adv. Mater.*, . 16:1440-4 (2004b).
Yang, et al., "A simple visual assay based on small molecule hydrogels for detecting inhibitors of enzymes," *Chem. Commun.*, 2424-25 (2004c).
Yang, et al., "Using a Kinase/Phosphatase Switch to Regulate a Supramolecular Hydrogel and Forming the Supramolecular Hydrogel in Vivo," *J. Am. Chem. Soc.*, 128:3038-43 (2006).
Zhang, et al., "Hydrogels: Wet or Let Die," *Nature Materials*, 3:7-8 (2004).
Zhang, et al., "Versatile small-molecule motifs for self-assembly in water and the formation of biofunctional supramolecular hydrogels", *Langmuir*, 27(2):529-37 (2011).
Gong, et al., "Synthesis of hydrogels with extremely low surface friction", J. Am. Chem. Soc., 123:,5582-3 (2001).

Gopinath, et al., "Ascorbyl palmitate vesicles (aspasomes): formation, characterization and applications", Intl J Pharma., 271(1-2):95-113 (2004).
International Search Report for corresponding PCT application PCT/US2016/056070 dated Jan. 12, 2017.
Peppas, et al., "Hydrogels in pharmaceutical formulations," Eur. J. Pharm. Biopharm., 50:27-46 (2000).
Sinha, et al., "Microbially triggered drug delivery to the colon", Eur. J. Pharm. Sci, 18:3-18 (2003).
van Esch and Feringa, "New functional materials based on self-assembling organogels: From serendipity towards design", Angew Chem Ltrs., 39(13):2263-6 (2000).
Yang, et al., "Enzymatic Formation of Supramolecular Hydrogels," Adv. Mater., 16:1440-4 (2004b).
Browne, et al., "Clinical outcome of autologous chondrocyte implantation at 5 years in US subjects", Clin Orthop Relat Res., 436:237-45 (2005).
Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J Materials Sci., 12:67-73 (2001).
Donati, et al.,"Synergistic effects im semidilute mixed solutions of alginate and lactose-midified chitosam (chitlac)", Biomacromolecules, 8:957-62 (2007).
European Search Report for EP 11827647 dated Jul. 16, 2014.
Hunziker, "Articular cartilage repair: basic science and clinical progress. A review of the current status and prospects", Osteoarthritis Cartilage, 10:432-63 (2002).
Indomethacin, MSDS product information, copywright Jun. 19, 2012.
International Search Report for PCT/US2009/057349 dated May 6, 2009.
International Search Report for PCT/US2011/053075 dated Apr. 17, 2012.
International Search Report for PCT/US2016/031614 dated Jul. 26, 2017.
International Search Report for PCT/US2017/031615 dated Sep. 25, 2017.
Kitagawa, et al., "Cationic Vesicles Consisting of 1,2-Dioleoyl-3-Trimethylammonium Propane (DOTAP) and Phosphatidylcholines and Their Interaction with Erythrocyte Membrane", Chem Pharma Bull., 52(4):451-3 (2004).
Krog and Sparse,"Food emulsifiers: their chemical and physical properties", Food Emulsions,Fourth Ed., pp. 45FF, CRC Press (2004).
Magnussen, et al., "Treatment of focal articular cartilage defects in the knee: a systematic review", Clin Orthop Relat Res, 466:952-96 (2008).
Marsich, et al., "Alginate/lactose-modified chitosan hydrogels: A bioactive biomaterial for chondrocyte encapsulation", J Biomat Mater Res A, 84(2):364-76 (2008).
Nishimura, et al., "Analysis of reducing end-groups produced by enzymatic scission of glycoside linkages in O-methylcellulose", Carbohydrate Res., 267:291-8 (1995).
Preliminary Report on Patentability for PCT/US2011/053075 dated Mar. 26, 2013.
Scogs, substances list, http://www.fda.gov/Food/IngredientsPackagingLabeling/GRAS/SCOGS/ucm084104.
Retrieved from interner Apr. 3, 2014.
Tomsic, et al., "Internally self-assembled thermoreversible gelling mulsions:ISAsomes in methylcellulose, k-carragrrnan, and mixed hydrogels", Langmuir, 25:9525 (2009).
Zhang, et al., "An inflammation-targeting hydrogel for local drug delivery in inflammatory bowel disease", Sci Transl Med., 7(300):300ra128 (2015).
Zhang, et al., "Self-assembled networks and molecular gels derived fro, long-chain, naturally-occurring fatty acids", J Brazilian Chem Soc., 239-55 (2016).

\* cited by examiner

STABILIZED ASSEMBLED NANOSTRUCTURES FOR DELIVERY OF ENCAPSULATED AGENTS

CROSS-REFERENCE TO RELATED APPLICATIONS

This application claims benefit of U.S. Provisional Application No. 62/239,211, filed Oct. 8, 2015, which is hereby incorporated herein by reference in its entirety.

STATEMENT REGARDING FEDERALLY SPONSORED RESEARCH OR DEVELOPMENT

This invention was made with Government support under grant no. R21DE023432 awarded by the National Institutes of Health. The Government has certain rights in the invention.

FIELD OF THE INVENTION

The disclosed technology is generally in the field of drug delivery employing low molecular weight, assembled nanostructures.

BACKGROUND OF THE INVENTION

Self-assembly in forming molecularly defined, high-ordered structures largely relies on non-covalent interactions. Structures formed from self-assembly are capable of entrapping molecules in solution during the assembly process, resulting in injectable carriers suitable for delivery of hydrophobic and hydrophilic agents.

However, self-assembled structures are generally unstable and are subject to biological, chemical, and mechanical perturbations. For example, the interactions of self-assembled structures with blood proteins are diverse and complex, often leading to dramatic effects on the stability and in vivo behavior of assembled structures. Serum lipoproteins may destabilize the amphiphilic building blocks of assembled structures by perturbing their hydrophobic-hydrophilic interactions. Irregularities at phase boundaries in the assembled structures may promote the destabilizing effects. (Bonte F and Juliano R L, *Chemistry and Physics of Lipids*, 40:359-372 (1986)). The disruption of assembled structures often leads to loss of contents and failure of therapeutic delivery.

Controlled release in response to pathological environments presents a significant challenge with self-assembled structures. The ability of drug delivery systems to reach target tissues from the point of administration can be limited by multiple barriers. For example, orally administered drug delivery systems must pass through the acid in the stomach, be absorbed across the intestinal epithelium, and avoid hepatic clearance and nonspecific uptake. Systemically administered, self-assembled materials are challenged with destabilization with blood proteins, loss of cargo, and rapid clearance from circulation.

Therefore, it is an object of the present invention to provide stabilized, self-assembled hydrogel or organo-gel formed with generally regarded as safe materials. It is another object of the present invention to provide stabilized self-assembled carriers for controlled release in response to biological stimuli.

It is yet another object of the present invention to provide a method of delivering active agents to disease sites with increased dosing efficacy and lower toxicity.

SUMMARY OF THE INVENTION

Gels including gelator and non-gelator amphiphiles can be co-assembled to form gels. These gels have nano and micro morphology, e.g. fibers under scanning electron microscopy ("SEM") are typically hundreds of nanometers across and tens to hundreds of microns long. These can be processed into particles which retain the nanostructures. Gels and gel particles are useful for delivery of therapeutic, prophylactic and/or diagnostic agents. Blood stabilized self-assembled hydrogel or organo-gel compositions have been developed. Low molecular weight (<2,500 Da) gelators which are generally regarded as safe (GRAS) or pharmaceutically acceptable are assembled into hydro- or organo-gel in the presence of stabilizing agent at an appropriate molar percentage. The assembly results in nano-scaled structures such as lamellae, micelle, vesicles, and fibers, forming the structural basis of the hydrogel or organo-gel. With the stabilizing agent, the composition can maintain at least 50, 60, 70 or 80% of its size or greater and/or not aggregate to twice the original size prior to exposure to the serum proteins for at least 30 minutes in the presence of serum proteins in phosphate buffered saline at 37° C. Unlike compositions without a stabilizing agent at an appropriate molar percentage (or molar fraction), the hydro-/organo-gel composition persists longer in the systemic circulation for at least one, two, four, twelve, or 24 hours. The stabilizing agent imparts rigidity and increases the packing density of the assembled nanostructures of the hydro-/organo-gel, thereby preventing or slowing down disruption by blood proteins of the assembled nanostructures. The stabilizing agent can be co-assembled with the gelators, or incorporated or intercalated into formed nanostructures. The stabilizing agent can also be entrapped in the assembled nanostructures.

The gelator is generally a low molecular weight GRAS compound, pharmaceutically acceptable or a pro-drug, which is labile in response to a biological stimulus such as enzymes, pH, and temperature and is generally capable being released as an active agent. Suitable gelators include ascorbyl alkanoate, sorbitan alkanoate, triglycerol monoalkanoate, sucrose alkanoate, glycocholic acid, and combinations thereof. Exemplary ascorbyl alkanoates include ascorbyl palmitate, ascorbyl decanoate ascorbyl laurate, ascorbyl caprylate, ascorbyl myristate, and ascorbyl oleate, which are hydrolyzable or enzyme cleavable to release ascorbic acid, i.e. vitamin C. A preferred gelator is ascorbyl palmitate. Exemplary sorbitan alkanoates include sorbitan monostearate, sorbitan decanoate, sorbitan laurate, sorbitan caprylate, sorbitan myristate, and sorbitan oleate. Exemplary triglycerol monoalkanoates include triglycerol monopalmitate, triglycerol monodecanoate, triglycerol monolaurate, triglycerol monocaprylate, triglycerol monomyristate, triglycerol monostearate, and triglycerol monooleate. Exemplary sucrose alkanoates include sucrose palmitate, sucrose decanoate, sucrose laurate, sucrose caprylate, sucrose myristate, and sucrose oleate.

An appropriate molar percentage of stabilizing agent in the assembled gel composition is at least 5, 10, 15, 20, 25, or 30 mole % to impart blood stability, where the size of the composition remains at least 50, 60, 70 or 80% or greater for at least 30 minutes, 1 hour, 2 hours, or 4 hours in blood. Suitable stabilizing agents include sterols, phospholipids, and low-molecular-weight therapeutic, prophylactic, or diagnostic agents. An exemplary sterol is cholesterol at about 10, 20, or 30 mole % as the stabilizing agent. An exemplary phospholipid is dipalmitoyl phosphatidyl glycerol at about 30, 40, or 45 mole % as the stabilizing agent.

Another exemplary stabilizing agent is a chemotherapeutic, docetaxel, at about 5, 6, 7, 8, 9, 10, 11, or 12 mole %.

One or more therapeutic, prophylactic, or diagnostic agents can be further included in the composition via encapsulation during the assembly process. While an agent in solution in its free form may have poor or no therapeutic efficacy, assembled gel based on the disclosed pro-drugs or GRAS compounds generally exhibits an enhanced therapeutic efficacy. For example, assembled composition based on ascorbyl palmitate has a half maximal inhibitory concentration ($IC_{50}$) of about 40-60 µM in inhibiting 4T3 murine breast cancer, whereas ascorbic acid in solution in this range of concentration may have no therapeutic efficacy. Included therapeutic, prophylactic, or diagnostic agent often exhibits an enhanced effect with the pro-drug or GRAS gelators in the composition, where a much lower dosage is needed for therapeutic benefits than the therapeutic, prophylactic, or diagnostic agent applied alone. For example, a chemotherapeutic drug, docetaxel, has an enhanced anti-cancer effect when delivered in ascorbyl palmitate-based assembled compositions. Possibly due to an enhanced permeability and retention (EPR) effect, the composition with nanostructures can preferentially accumulate in tumors. Compared with agents delivered in the absence of the assembled composition, the composition generally has a greater partition in tumor compared to in liver.

The blood stabilized self-assembled hydrogel or organogel composition may be administered in combination with pharmaceutically acceptable excipient. It may also be in a dosage unit supplied in a kit, where dry components and liquid components are separately contained and mixed upon administration to a subject for in situ gelation.

A method to prepare the blood-stabilized, self-assembled hydro- or organo-gel composition has also been developed. A gelator, a stabilizing agent, and an optional agent to be encapsulated are first dissolved in an appropriate solvent such as dimethyl sulfoxide (DMSO), methanol, ethanol, hexane, isopropanol, and water. The material is heated to an appropriate temperature, outside or in the range of 60-80° C. until full dissolution, followed by cooling to about room temperature. An amount of water, e.g., ultrapure water, is subsequently added, and the material is heated to an appropriate temperature until full dissolution. Gelation generally occurs after about 15-45 minutes. The gel can be suspended in ultrapure water and resuspended in ultrapure water and pulse sonicated.

The bulk gel includes at least portion of material with nanostructured morphology. The bulk gel can be broken into gel particles. The morphology of the gels is preserved in particles. Particle size and aggregation can be used as a measure of stability. The goal is not to have significant decreases in size, nor aggregation (i.e., increases in size). Particles typically have irregular morphology and often look like fibers.

The composition can be used to deliver a therapeutic, prophylactic, or diagnostic agent to a subject for controlled release. These can be administered systemically by intravenous injection, infusion, topically, and implantation.

BRIEF DESCRIPTION OF THE DRAWINGS

FIG. 11A shows the fluorescence intensity of the dye in different tissues. FIG. 11B shows the ratio of fluorescence in tumor to fluorescence in liver.

DETAILED DESCRIPTION OF THE INVENTION

I. Definitions

Figures 1A, 1C:
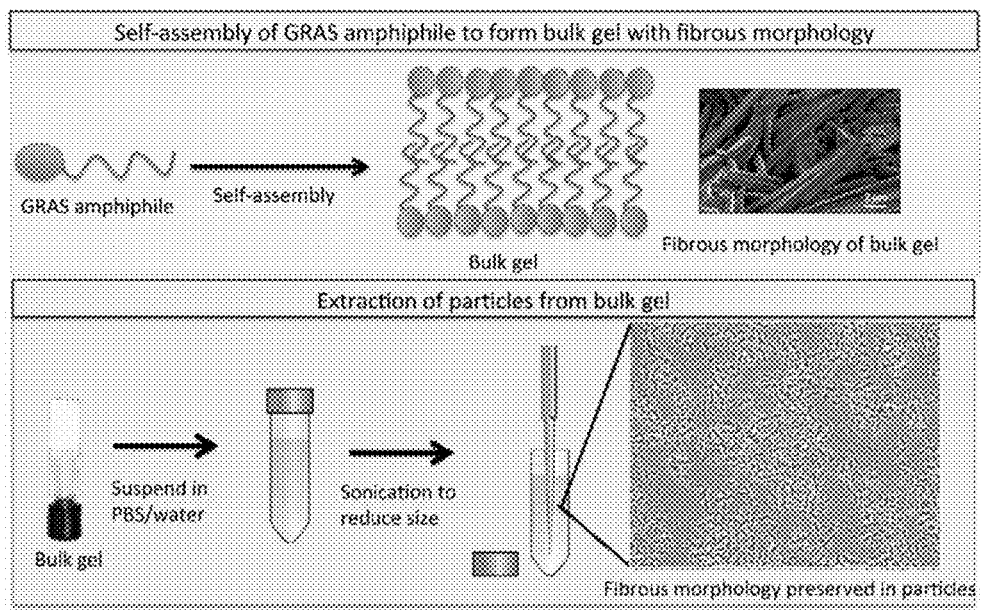
FIG. 1A is a schematic showing self-assembly of GRAS amphiphiles to form bulk gels that have fibrous morphology.
FIG. 1C is a schematic showing extraction of particles from bulk gel.

The term "gelators" refer to molecules that can self-assemble through non-covalent interactions, such as hydrogen-bonding, van der Waals interactions, hydrophobic interactions, ionic interactions, pi-pi stacking, or combinations thereof, in one or more solvents. The gelators can form a gel by rigidifying the solvent through, for example, capillary forces. Gelators can include hydrogelators (e.g., gelators that form hydrogels) and organo-gelators (e.g., gelators that form organo-gels). In some embodiments, gelators can form both hydrogels and organo-gels.

The term "self-assembling" refers to the capability of molecules to spontaneous assemble, or organize, to form a high ordered structure such as hydrogel or organo-gel in a suitable environment.

The term "hydrogel" refers to 3-D networks of molecules typically covalently (e.g., polymeric hydrogels) or non-covalently (e.g., self-assembled hydrogels) held together where water is the major component (usually greater than 80%). Gels can be formed via self-assembly of gelators or via chemical crosslinking of gelators. Water-based gelators can be used to form hydrogels, whereas organo-gelators are gelators that form gels (organo-gels, or organo-gels) in solvents where organic solvents are the major component.

The term "organo-gel" refers to 3-D networks of molecules typically covalently (e.g., polymeric hydrogels) or non-covalently (e.g., self-assembled hydrogels) held together where an organic solvent is the major component (usually greater than 80%). Gels can be formed via self-assembly of gelators or via chemical crosslinking of gelators.

The term "therapeutic agent" refers to an agent that can be administered to prevent or treat one or more symptoms of a disease or disorder or dysfunction.

The term "diagnostic agent" generally refers to an agent that can be administered for purposes of identification or imaging.

The term "prophylactic agent" generally refers to an agent that can be administered to prevent disease or to prevent certain conditions like pregnancy.

The term "prodrug" refers to a drug, drug precursor of modified drug that is not fully active or available until converted in vivo or in situ to its therapeutically active or available form.

"Blood" refers to the cellular suspension that circulates within an animal to deliver nutrients and gases, as well as the cells therein. "Serum" is the liquid remaining after the blood is clotted, and the fibrin clot and cellular material is removed. "Plasma" is the acellular component of the blood. The protein content of blood, plasma and serum are different, but most proteins are common to all three.

II. Composition

1. Gelator

Gelators are amphiphilic molecules which self-assemble to form gel compositions with nanofibrous structures. In a preferred embodiment, these are GRAS materials generally less than 2,500 Da in molecular weights.

In some embodiments, the GRAS gelators can include ascorbyl alkanoate, sorbitan alkanoate, triglycerol monoalkanoate, sucrose alkanoate, glycocholic acid, or any combination thereof. The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester, a carbamate, a thioester and an amide linkage) to an ascorbyl, sorbitan, triglycerol, or sucrose molecule. For example, the ascorbyl alkanoate can include ascorbyl palmitate, ascorbyl decanoate, ascorbyl laurate, ascorbyl caprylate, ascorbyl myristate, ascorbyl oleate, or any combination thereof. The sorbitan alkanoate can include sorbitan monostearate, sorbitan decanoate, sorbitan laurate, sorbitan caprylate, sorbitan myristate, sorbitan oleate, or any combination thereof. The triglycerol monoalkanoate can include triglycerol monopalmitate, triglycerol monodecanoate, triglycerol monolaurate, triglycerol monocaprylate, triglycerol monomyristate, triglycerol monostearate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof. In some embodiments, the GRAS gelators include ascorbyl palmitate, sorbitan monostearate, triglycerol monopalmitate, sucrose palmitate, or glycocholic acid.

Representative low molecular weight GRAS gelators include vitamin precursors such as ascorbyl palmitate (vitamin C precursor), retinyl acetate (vitamin A precursor), and alpha-tocopherol acetate (vitamin E precursor).

In some embodiments, instead of or in addition to a GRAS first gelator, the self-assembled gel compositions can be formed of amphiphilic 3-aminobenzamide derivatives including a molecular weight of 2,500 or less. The gelator can also be or include a prodrug that can transform to the active form of the drug in physiological conditions.

In other embodiments, one or more saturated or unsaturated hydrocarbon chains having $C_1$ to $C_{30}$ groups is synthetically modified onto a low molecular weight, generally hydrophilic compound, through esterification or a carbamate, anhydride, and/or amide linkage. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ etc. up to $C_{30}$ as wells as ranges falling within $C_1$ to $C_{30}$, for example, $C_1$ to $C_{29}$, $C_2$ to $C_{30}$, $C_3$ to $C_{28}$, etc.

In some embodiments, alpha tocopherol acetate, retinyl acetate, retinyl palmitate, or a combination thereof, can co-assemble with the gelators.

2. Degradable Linkages

Stimuli evoking release can be present due to the characteristics at the site of administration or where release is desired, for example, tumors or areas of infection. These may be conditions present in the blood or serum, or conditions present inside or outside the cells, tissue or organ. The gel compositions may be designed to disassemble only under conditions present in a disease state of a cell, tissue or organ, e.g., inflammation, thus allowing for release of an agent at targeted tissue and/or organ.

For example, the gel compositions can include degradable linkages that are cleavable upon contact with an enzyme and/or through hydrolysis, such as ester, amide, anhydride, a thioester, and carbamate linkages. Typically, linkage is always between hydrophilic and hydrophobic parts of the amphiphile molecule. In some embodiments, phosphate-based linkages can be cleaved by phosphatases. In some embodiments, labile linkages are redox cleavable and are cleaved upon reduction or oxidation (e.g., —S—S—). In some embodiments, degradable linkages are susceptible to temperature, for example cleavable at high temperature, e.g., cleavable in the temperature range of 37-100° C., 40-100° C., 45-100° C., 50-100° C., 60-100° C., 70-100° C. In some embodiments, degradable linkages can be cleaved at physiological temperatures (e.g., from 36 to 40° C., about 36° C., about 37° C., about 38° C., about 39° C., about 40° C.). For example, linkages can be cleaved by an increase in temperature. This can allow use of lower dosages, because agents are only released at the required site. Another benefit is lowering of toxicity to other organs and tissues. In certain embodiments, stimuli can be ultrasound, temperature, pH, metal ions, light, electrical stimuli, electromagnetic stimuli, and combinations thereof.

3. Stabilizing Agent

Agents enhancing blood stability and/or reducing the rate of disassembly of nanostructures after administration are included in the composition. Blood proteins including albumin can interact with irregularities in the assembled lamellar, micellar, vesicular, and/or fibrous structures, such as those that exist at the phase boundaries, resulting in a higher rate of disassembly of particles or the higher structured nanoparticles or bulk hydrogel. Stabilizing agents typically impart rigidity, increase the packing density, and/or enhance the strength of assembled structures, thus altering the phase transition process and transitioning temperature, and/or modulating the surface properties of assembled particles to reduce or prevent protein adhesion or accumulation.

Generally, the stabilizing agents diminish the rate of reduction in the size of the assembled particles or nanoparticles when placed in a serum solution, whereas compositions without stabilizing agents substantially decrease the hydrodynamic size in serum solutions in about 30 minutes. Stabilizing agents allow for more than 50%, 60%, 70%, 80%, 90%, 95%, 99% of the assembled nanostructures to have less than 1%, 5%, 10%, 15%, 20%, or 30% reduction in the hydrodynamic sizes in at least one, two, three, four, 12, 24, or 48 hours in incubation with serum at 37° C.

In general, the molecules that can rigidify the self-assembled lamellae will usually be hydrophobic molecules, molecules that can change surface properties, like small chain hydrophilic polymers, and/or molecules that can modify the surface charge (charged molecules).

In some embodiments, the stabilizing agents are co-assembled with gelators in the formation of assembled gel compositions. These stabilizing agents are generally incorporated into the lamellar, micellar, vesicular, and/or fibrous structures by encapsulation, integrated, entrapment, insertion or intercalation. Generally, inclusion of 10-30 mole % of co-assembly type, stabilizing agents allows for the assembled nanoparticles to maintain about 80% or more of the original size when incubated over a period of two to four hours in serum solutions.

Exemplary stabilizing agents include sterols, phospholipids, and low molecular weight therapeutic compounds that are typically hydrophobic. Suitable sterols include cholesterol, corticosteriods such as dihydrocholesterol, lanosterol, β-sitosterol, campesterol, stigmasterol, brassicasterol, ergocasterol, Vitamin D, phytosterols, sitosterol, aldosterone, androsterone, testosterone, estrogen, ergocalciferol, ergosterol, estradiol-17alpha, estradiol-17beta, cholic acid, corticosterone, estriol, lanosterol, lithocholic acid, progesterone, cholecalciferol, cortisol, cortisone, cortisone acetate, cortisol acetate, deoxycorticosterone and estrone, and fucosterol. Other stabilizing agents include, but are not limited to, lysophospholipids (including lyso PC, 2-hexadecoxy-oxido-phosphoryl)oxyethyl-trimethyl-azanium), gangliosides, including GM1 and GT1b, sulfatide, sphingophospholipids, synthetic glycopholipids such as sialo-lactosyl, phospholipids, including DOPE, DOPS, POPE, DPPE, DSPE, lipophilic drugs such as cytosine arabinoside diphosphate diacyglycerol, proteins such as cytochrome b5, human high density lipoprotein (HDL), human glycophorin A, short chain hydrophilic polymers, including polyethylene glycol (PEG) and their derivatives with lipids, bile acids include taurocholic acid, desoxycholic acid, and geicocholic acid, 1,1'-dioctadecyl 3,3,3',3'-tetramethyl-indocarbocyanine percholorate (DiI), DiR, DiD, fluorescein isothiocyanate, tetramethylrhodamine isothiocyanate, rhodamine B octadecyl ester perchlorate and N'-Octadecylfuorescein-5-thiourea. Sterols generally co-assemble with one or more gelators, inserting into the ordered lamellar, micellar, vesicular, and/or fibrous structures. Sterols by themselves are not gelators and cannot form gel compositions on their own.

Suitable phospholipids include dipalmitoyl phosphatidyl choline and distearoyl phosphatidyl choline. The phospholipids typically co-assemble with one or more gelators in forming the ordered lamellar and/or fibrous structures.

In other embodiments, the stabilizing agents are an agent encapsulated in the assembled composition, typically throughout the gel composition, rather than insertion or intercalation into the lamellar, micellar, vesicular, and/or fibrous structures. Generally, inclusion of between 5 and 15 mole % stabilizing agents allows for the assembled nanostructures to maintain about 80% or more of the original size when incubated over a period of two to four hours in serum solutions.

In some embodiments, therapeutic, prophylactic and/or diagnostic agents may diminish reduction in the size of the assembled nanoparticles when placed in a blood or serum solution, where more than 50%, 60%, 70%, 80%, 90%, 95%, 99% of the nanostructures in incubation with serum at 37° C. have less than 1%, 5%, 10%, 15%, 20%, or 30% reduction in the hydrodynamic sizes in at least one, two, three, four, 12, 24, or 48 hours, compared to gel composition without the active agents. An exemplary hydrophobic, chemotherapeutic agent, docetaxel, may stabilize the nanostructures formed from gelators when encapsulated at a molar percentage of 2%, 4%, 6%, 8%, and 10%, and all values in the range, between the active agent and the gelators.

Suitable low molecular weight therapeutic, prophylactic and/or diagnostic agents used as stabilizing agents for the gel compositions are generally hydrophobic, of a low molecular weight (e.g., less than 2,500 Da), such as docetaxel and steroids and other hydrophobic agents such as dexamethasone, or a combination of agents.

4. Therapeutic, Prophylactic, and Diagnostic Agents

The assembled gel compositions can be used to deliver one or more therapeutic, prophylactic or diagnostic agents to an individual or subject in need thereof. Therapeutic, prophylactic and diagnostic agents may be proteins, peptides, sugars or polysaccharides, lipids or lipoproteins or lipopolysaccharids, nucleic acids (DNA, RNA, siRNA, miRNA, tRNA, piRNA, etc.), or small molecules (typically 2000 D or less, more typically 1000 D or less, organic, inorganic, natural or synthetic).

Gelators may be prodrugs that hydrolytically or enzymatically degrade and release active agents. The therapeutic, prophylactic, or diagnostic agents may be physically entrapped, encapsulated, or non-covalently associated with the nanofibrous structures of the gel composition. The therapeutic, prophylactic, or diagnostic agents may be covalently modified with one or more gelators, one or more stabilizers, or be used as a gelator. Alternatively, they are incorporated into the assembled ordered lamellar, vesicular, and/or nanofibrous structures of the gel composition or positioned on the surface of the assembled structures.

The assembled nanostructures can also be used to co-deliver multiple agents, thereby resulting in their synergistic or additive effects and generally less required dosage for therapeutic efficacy. Synergy can be achieved by encapsulating the active agent in pro-drug based particles, e.g. ones made with gelators including vitamin C, vitamin K and their derivatives, by co-entrapping multiple agents, by co-delivering other sensitizing molecules, or a combination thereof.

Both hydrophobic and hydrophilic agents can be encapsulated into these particles with high encapsulation and loading efficiencies, and remain stably encapsulated in normal physiological conditions. The encapsulated agents can include, for example, anti-inflammatory drugs, steroids, antibiotics, immunosuppressants, chemotherapeutics, sensitizing agents, antibodies, antibody fragments, proteins, peptides, growth factors, cytokines, cells, stem cells, nucleic acids, siRNA, vitamins etc. and a combination thereof.

Exemplary therapeutic and prophylactic agents include proteins or peptides, sugars or polysaccharides, lipids, nucleic acids, or combinations thereof. In a preferred embodiment, these are small molecules, generally having a molecular weight of 2000 Daltons or less, more preferably 1000 Daltons or less. Exemplary classes of therapeutic agents include, but are not limited to, anti-proliferatives such as anti-cancer agents, anti-angiogenesis agents, and anti-mitotic agents, analgesics, anti-inflammatory drugs, antipyretics, antiepileptics, antipsychotic agents, neuroprotective agents, anti-infectious agents, such as antibacterial, antiviral and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, gastro-intestinal drugs, muscle relaxants, parasympathomimetics, stimulants, anorectics and anti-narcoleptics.

Preferred classes of small molecules to include in the protein nanocages include cancer therapeutics such as chemotherapeutic agents, cytokines, chemokines, and radiation therapy enhancers. The majority of chemotherapeutic drugs can be divided into: alkylating agents, antimetabolites, anthracyclines, plant alkaloids, topoisomerase inhibitors, and other antitumor agents. All of these drugs affect cell division or DNA synthesis and function in some way. Additional therapeutics include monoclonal antibodies (including fragments thereof) and tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

Exemplary therapeutic agents include chemotherapeutic and antitumor agents. Representative chemotherapeutic agents include, but are not limited to, docetaxel, doxorubicin, dexrazoxane, sorafenib, erlotinib hydrochloride, platinum containing drugs such as cisplatin, cetuximab, sunitinib, bevacizumab carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab, rituximab and combinations thereof.

In some embodiments, the agent is one or more nucleic acids. The nucleic acid can alter, correct, or replace an endogenous nucleic acid sequence. The nucleic acid is used to treat cancers, correct defects in genes in other diseases and metabolic diseases affecting mucus-covered tissues, genes such as those for the treatment of Parkinson's and ALS where the genes reach the brain through nasal delivery. One example is MACUGEN® (pegaptanim sodium, anti-VEGF aptamer or EYEOO1) (Eyetech Pharmaceuticals).

Gene therapy is a technique for correcting defective genes responsible for disease development. There are several approaches for correcting faulty genes. A normal gene may be inserted into a nonspecific location within the genome to replace a nonfunctional gene. An abnormal gene could be swapped for a normal gene through homologous recombination. The abnormal gene could be repaired through selective reverse mutation, which returns the gene to its normal function. The regulation (the degree to which a gene is turned on or off) of a particular gene could be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to, use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linkage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Therapeutic protein, protein fragments, peptides or related compounds include antibodies to vascular endothelial growth factor (VEGF) such as bevacizumab (AVASTIN®) and rhuFAb V2 (ranibizumab, LUCENTIS®), and other anti-VEGF compounds; pigment epithelium derived factor(s) (PEDF); interferon alpha; interleukin-12 (IL-12); endostatin; angiostatin; ribozyme inhibitors such as ANGIOZYME® (Sirna Therapeutics); multifunctional anti-angiogenic agents such as NEOVASTAT® (AE-941) (Aeterna Laboratories, Quebec City, Canada; antibodies to the epidermal grown factor receptor such as panitumumab (VECTIBIX®) and cetuximab (ERBITUX®), as well as other anti-angiogenesis agents known in the art.

Other small molecules that can be delivered include COX-2 inhibitors such as celecoxib (CELEBREX®) and rofecoxib (VIOXX®); thalidomide (THALOMID®) and derivatives thereof such as lenalidomide (REVLIMID®); squalamine;); receptor tyrosine kinase (RTK) inhibitors such as sunitinib (SUTENT®); tyrosine kinase inhibitors such as sorafenib (Nexavar®) and erlotinib (Tarceva®).

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radiopaque. Protein nanocages can further include agents useful for determining the location of administered nanocages. Agents useful for this purpose include fluorescent tags, radionuclides and contrast agents.

5. Formulations

Liquid Formulations

Liquid formulations contain one or more assembled particles suspended in a liquid pharmaceutical carrier.

Suitable liquid carriers include, but are not limited to, distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

Formulations may be prepared using one or more pharmaceutically acceptable excipients, including diluents, preservatives, binders, lubricants, disintegrators, swelling agents, fillers, stabilizers, and combinations thereof. Liquid formulations may also contain minor amounts of polymers, surfactants, or other excipients well known to those of the art. In this context, "minor amounts" means no excipients are present that might adversely affect the delivery of assembled gel compositions to targeted tissues, e.g. through circulation.

Dry Powder Formulations and Kit

In some forms, the gelators, stabilizing agents, and optionally one or more therapeutic, prophylactic, and diagnostic agents are formulated in dry powder forms as finely divided solid formulations. The dry powder components can be stored in separate containers, or mixed at specific ratios and stored. In some embodiments, suitable aqueous and organic solvents are included in additional containers. In some embodiments, dry powder components, one or more solvents, and instructions on procedures to mix and prepare assembled nanostructures are included in a kit. Alternatively, stabilized, assembled particles, nanoparticles or bulk gel thereof are dried via vacuum-drying or freeze-drying, and suitable pharmaceutical liquid carrier can be added to rehydrate and suspend the assembled nanostructures or gel compositions upon use.

Dry powder formulations are typically prepared by blending one or more gelators, stabilizing agents, or active agents with one or more pharmaceutically acceptable carriers. Pharmaceutical carrier may include one or more dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

The dry powder formulations can be suspended in the liquid formulations to form assembled particles or nanoparticles thereof, and administered systemically or regionally using methods known in the art for the delivery of liquid formulations.

Injectable Formulations

In some embodiments, the stabilized, assembled particles are formulated for parenteral delivery, such as injection or infusion, in the form of a solution or suspension. The formulation can be administered via any route, such as, the blood stream or directly to the organ or tissue to be treated. For example, parenteral administration may include administration to a patient intravenously, intradermally, intraperitoneally, intrapleurally, intratracheally, intramuscularly, subcutaneously, subjunctivally, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized gelators, stabilizing agents, and/or active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzyl peroxide, benzethonium chloride, benzyl alcohol, cetylpyridinium chloride, chlorobutanol, phenol, phenylethyl alcohol, and thimerosal.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. These preferably are enteric coated to avoid disassembly when passing through the stomach Excipients, including plasticizers, pigments, colorants, stabilizing agents, and glidants, may also be used to form coated compositions for enteral administration. Formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

III. Method of Making

1. Making Hydrogel or Organo-Gel Nanostructures

Figure 1B:
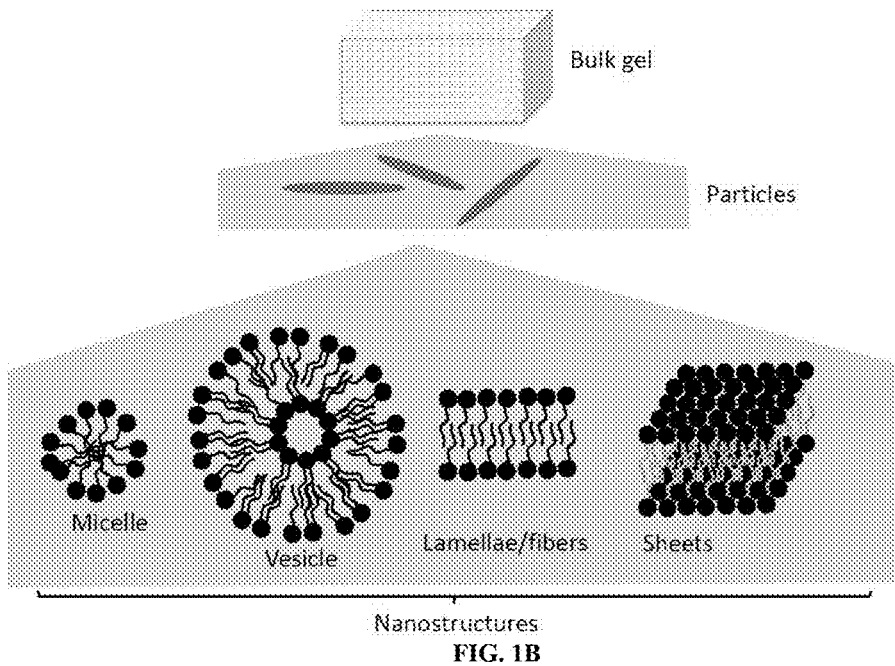
FIG. 1B is a schematic summarizing the co-self assembly of nanostructures in bulk gel and particles derived therefrom.
Figures 2A, 2B, 2C, 2D:
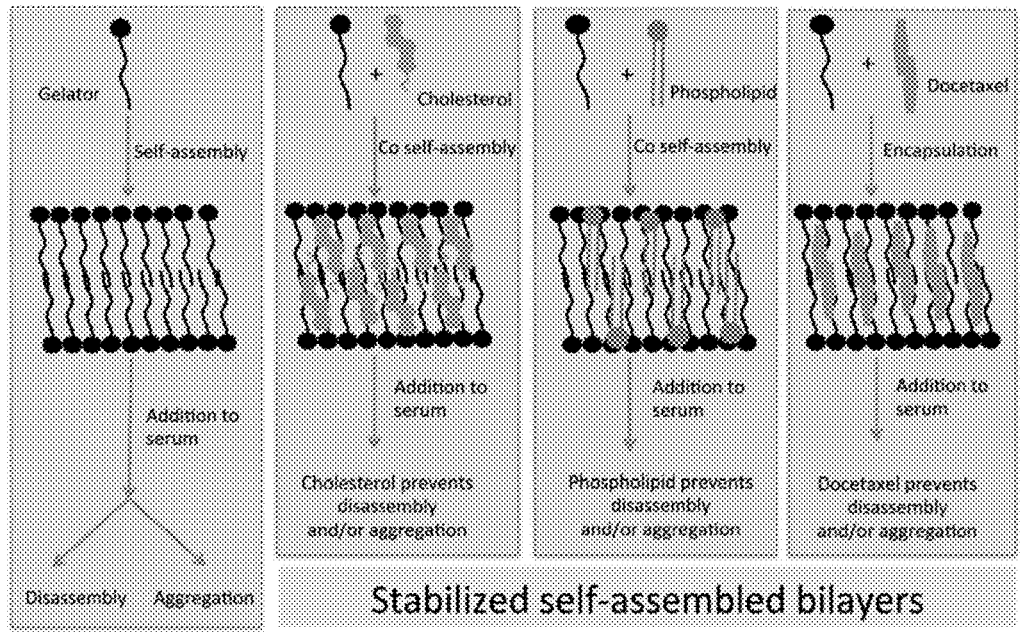
FIGS. 2A-2D are schematics summarizing the co-self assembly and encapsulation of serum stabilizing agents in GRAS gels to obtain serum stable particles: 2A, gelation and self-assembly; 2B, incorporation of cholesterol into the nanostructures; 2C, incorporation of phospholipid into nanostructures; and 2D, incorporation of docetaxel.

FIG. 1A is a schematic showing self-assembly of GRAS amphiphiles to form bulk gels that have fibrous morphology. FIG. 1B shows that the self-assembly in the bulk gel or particles can have a variety of shapes, including micelles, vesicles, lamellae or fibers, sheets, tapes, etc. Generally, as shown in FIG. 1A, to form a stabilized, self-assembled gel composition, a solvent, a gelator, a stabilizing agent, and optionally an agent to be encapsulated, are added to a container to form a mixture. In some embodiments, the mixture can include one or more solvents (e.g., a polar solvent such as dimethyl sulfoxide (DMSO), methanol, isopropanol, hexane, or water), one or more gelators (e.g., GRAS gelators), one or more stabilizing agents, and/or one or more agents to be encapsulated. The mixture can be heated and/or sonicated and/or placed in a bath to completely dissolve the gelator to form a homogeneous solution, and the solution is then cooled and/or rested in an undisturbed location. The solution can transition into a viscous gel after a given time period. Gelation is deemed complete when no gravitational flow is observed upon inversion of the container.

To remove an unencapsulated agent from the gels, water or a solvent that can dissolve the agent but not gel particles can be added to the gels and particles dispersed solution can be repeatedly vortexed. The supernatant solution can be removed to extract any unencapsulated agent.

When the stabilized, self-assembled gel compositions do not include a solvent, a gelator can be combined with a liquid amphiphile (e.g., a vitamin-derived liquid amphiphile) to form a mixture. The mixture can include one or more gelators, one or more stabilizing agents, and one or more liquid amphiphiles. The mixture is then heated/sonicated/placed in a bath to form a homogenous solution. The resulting solution is then allowed to cool and/or rest in an undisturbed location. The solution can transition into a viscous gel after a given time period.

In some embodiments, one or more gelators and optionally an agent to be encapsulated can be combined in the absence of a solvent to form a mixture. The mixture is then heated/sonicated/placed in a bath to form a homogenous solution. The resulting solution is then allowed to cool and/or rest in an undisturbed location. The solution can transition into a viscous gel after a given time period.

In some embodiments, to encapsulate an agent, a melted gel including one or more gelator and one or more solvents can be added to a solid agent, to an agent dissolved a the same one or more solvents, or to an agent dissolved or suspended in a gel-compatible solvent.

In some embodiments, the heating temperatures can be from 40 (e.g., from 50, from 60, from 70, from 80, from 90, or from 100) to 110 (e.g., to 100, to 90, to 80, to 70, to 60, or to 50) ° C., depending on the temperature sensitivity of the gelators, stabilizing agents, and/or active agents. These mixtures can be heated and/or sonicated and/or placed in a bath for a duration of from one (e.g., from five, from 10, from 15, from 20, or from 25) to 30 (to 25, to 20, to 15, to 10, or to five) minutes or longer until all material is dissolved. The solutions are cooled to a temperature of from 4 (e.g., from 10, from 20, or from 25) to 37 (e.g., to 25, to 20, or to 10) ° C. and/or rested for a duration of from 15 minutes (e.g., from 30 minutes, from 45 minutes) to one hour (e.g., to 45 minutes, to 30 minutes).

In some embodiments, the nanostructures (e.g., fibers, sheets, FIG. 1B) can have a length and/or width of several microns (e.g., one micron, two microns, three microns, four microns, five microns, ten microns, twenty microns, or twenty five microns) or more. The nanostructures can aggregate into networks, and/or be in the form of a liquid crystal, emulsion, fibrillar structure, or tape-like morphologies. When the nanostructures are in the form of fibers, the fibers can have a diameter of about 2 nm or more, and can have lengths of hundreds of nanometers or more. In some embodiments, the fibers can have lengths of several microns (e.g., one micron, two microns, three microns, four microns, five microns, ten microns, twenty microns, or twenty five microns) or more.

When amphiphilic molecules self-assemble in a solvent, hydrophobic and hydrophilic portions of the gelator molecules can interact to form lamellae of gelator molecules. In some embodiments, when the gels are hydrogels, the hydrophobic portions of gelators are located in the inner regions of a given lamella, and hydrophilic portions are located at the outer surfaces of the lamella. In some embodiments, when the gels are organo-gels, the hydrophobic portions of gelators are located in the outer regions of a given lamella, and hydrophilic portions are located at the inner surfaces of the lamella. The lamella can have a width of from about three (e.g., from about four) to about five (e.g., to about four) nanometers and a length of several microns (e.g., one micron, two microns, three microns, four microns, five microns, ten microns, twenty microns, or twenty five microns) or more. Several tens or hundreds of such lamellae can bundle together to form nanostructures, such as fibers of nano-sized width (e.g. 100-900 nm with lengths of several microns or longer) and sheet-like structures.

2. Encapsulation of Agents to be Delivered and Stabilizing Agents

FIGS. 2A-2D are schematics summarizing the co-self assembly and encapsulation of serum stabilizing agents in GRAS gels to obtain serum stable particles. Low molecular weights GRAS or pro-drug gelators, stabilizing agents, and optionally therapeutically active agents are dissolved in a water-miscible organic solvent, and optionally either water or phosphate buffer saline (PBS) is added to the mixture. The gelators can be at least 10 mole %, 20 mole %, 30 mole %, 40 mole %, 50 mole %, 60 mole %, 70 mole %, 80 mole %, or 90 mole % of the total amount of gelators, stabilizing agents, and therapeutically active agents. The gelators are dissolved in the solvent to between 0.01 and 50 wt % (e.g., up to 500 mg/mL). The stabilizing agents can be added to 3 mole %, 4 mole %, 5 mole %, 6 mole %, 7 mole %, 8 mole %, 9 mole %, 10 mole %, 15 mole %, 20 mole %, 30 mole %, or 40 mole % of the total amount of gelators, stabilizing agents, and therapeutically active agents, depending on the type of stabilizing agents. For stabilizing agents that co-assemble with gelators, the mole percentage of stabilizing agents in the total amount of gelators and stabilizing agents can be between about 10 mole % and about 40 mole %, preferably between about 20 mole % and about 35 mole %, and most preferably about 30 mole %.

3. Processing into Particles

In some embodiments, the self-assembled gel is isolated through repeated cycles of centrifugation (e.g., 2,000-25,000 rpm for 2-15 minutes), PBS washings, and/or pulse sonication (e.g., 5-50 kHz, 10%-50% amplitude, for 0.5-10 minutes) to provide water dispersible self-assembled nanostructures or to remove unencapsulated agents from pelleted gel. FIG. 1C is a schematic showing the formation of particles from bulk gel. The bulk gel is suspended in water and/or phosphate buffered saline ("PBS") and sonicated to break up the bulk gel into particles which retain the fibrous nanostructures formed in the bulk gel In some embodiments, the nanostructures can have a minimum dimension (e.g., a thickness, a width, or a diameter) of 2 nm or more (e.g., 50 nm or more, 100 nm or more, 150 nm or more, 200 nm or more, 250 nm or more, 300 nm or more, 350 nm or more) and/or 400 nm or less (e.g., 350 nm or less, 300 nm or less, 250 nm or less, 200 nm or less, 150 nm or less, 100 nm or less, or 500 nm or less) when measured in a dry environment such as the vacuum dried sample in scanning electron microscopy; or a minimum dimension of 10 nm, 50 nm, 100 nm, 200 nm, 300 nm, 400 nm, 500 nm or more when measured for hydrodynamic sizes via dynamic light scattering.

The nanoparticles can have a hydrodynamic diameter between 100 nm and 990 nm, preferably between 500 nm and 900 nm, and the nanoparticles maintain at least 50, 60, 70 or 80% of the size in serum over a period of at least two hours.

IV. Methods of Using

The stabilized, assembled nanostructures (in any form, including nanoparticles) have enhanced stability in blood against disassembly by blood proteins, compared to nanostructures or nanostructures not including stabilizing agents. The composition can be administered parentally, for example, by injection intravenously, intradermally, intraperitoneally, intrapleurally, intratracheally, intramuscularly, subcutaneously, subjunctivally, by infusion, topically, or implanted.

The stabilized gel compositions can be controllably disassembled, for example, upon exposure to hydrolytic or enzymatic degradation, or by exposure to an external stimulus. Gels can be disassembled by cleavage of a labile linkage in an amphiphilic gelator, such as an ester, amide, anhydride, carbamate, phosphate-based linkages (e.g., phosphodiester), disulfide (—S—S—), acid-cleavable groups such as —OC(O)—, —C(O)O—, or —C=NN— that can be present between a hydrophobic and hydrophilic group within the gelator. Examples of labile linkages are also described, for example, in PCT publication WO2010/033726.

In some embodiments, encapsulated agents can be controllably released from the gel compositions upon gel disassembly. For example, encapsulated agents can be gradually released over a period of time (e.g., a day, a week, a month, six months, or a year). Depending on the parameters, release can be delayed or extended from minutes to days to months, for example, when gel compositions are administered under physiological conditions (a pH of about 7.4 and a temperature of about 37° C.).

Different parameters can be used to control release. For example, sustained release can be controlled by the concentration of an enzyme and/or a temperature. Release can be accelerated using a high enzyme concentration, for example, by delivery to an area of infection, characterized by elevated enzyme concentrations, or low pH, for example, in tumors or areas of infection. In some embodiments, the sustained release occurs without a burst release, or with only a minimal burst release.

With the enhanced stability in blood and other bodily fluids against protein disassembly and the controlled released of drug or encapsulated active agents, the gel compositions or nanofibrous particles can be used to provide a controlled delivery of drugs or active agents in therapeutic amounts for an extended period of time (e.g., an hour, two hours, four hours, twelve hours, a day, a week, or longer).

In a preferred embodiment, the stabilized, assembled gel compositions or nanofibrous particles are used to deliver one or more active agents into the tumor tissues for sustained delivery of chemotherapeutics, and even uptake by tumor cells. Tumor cells produce esterases, and inflamed tissues release enzymes, both of which provide pathology-specific degradation of pro-drug gelators and release of active agents. Compared with active agents delivered in its free forms, the stabilized, assembled compositions partition in tumor tissues, i.e., accumulate in tumor tissues more than in non-tumor tissues, following systemic administration.

Alternatively, the gelators can be applied to a biological system and self-assembly can occur in situ. For example, the gel compositions described herein may be applied to the surface of bone and the gel can be assembled within the pores of the bone. For example, heated gel compositions can be injected in solution form to a bone site, which can then cool to physiological temperatures to assemble into gel forms.

The stabilized gel compositions or nanofibrous particles can be useful for improving targeting efficiency, efficacy, safety, and compliance benefiting from single dose, prolonged action or tissue-specific formulations, compared to non-stabilized gel compositions, assembled nanostructures, and delivery of active agents in its free form. Exemplary diseases or disorders to be treated with the stabilized assembled nanostructures include, but are not limited to, allergy (e.g. contact dermatitis), arthritis, asthma, cancer, cardiovascular disease, diabetic ulcers, eczema, infections, inflammation, mucositis, periodontal disease, psoriasis, respiratory pathway diseases (e.g., tuberculosis), vascular occlusion, pain, graft versus host diseases, canker sores, mucositis, bacterial conditions, viral conditions.

The stabilized assembled nanostructures and gel compositions can also be administered through various known regional delivery techniques, including injection, implantation, inhalation using aerosols, and topical application to the mucosa, such as the oral or buccal surfaces, nasal or pulmonary tracts, intestinal tracts (orally or rectally), vagina, or skin. In situ self-assembly of stabilized nanostructures allows for regional delivery of the compositions and stimuli-responsive delivery of active agents. When tumor cells produce esterases or inflamed tissues release enzymes, the enzyme disassembles gel compositions, which releases active agents such as anti-inflammatory, anti-proliferative or chemotherapeutic agents. After the agent is released, the enzyme concentration decreases. The gel compositions that are not cleaved remain stable, until another inflammatory stimulus for "on-demand release", where the pathological environment regulates the amount and timing of an agent release. In some embodiments, the compositions can be useful to release therapeutic agents that correlate with different stages of tissue regeneration.

The present invention will be further understood by reference to the following non-limiting examples.

EXAMPLES

Example 1. Assembly of Blood-Stabilized Gels

Methods and Materials

The first step involved the dissolution of gelator (ascorbyl palmitate), stabilizer (cholesterol) and the agent to be encapsulated (docetaxel, DTX, or a dye) in an appropriate solvent, e.g., a polar solvent such as dimethyl sulfoxide (DMSO), methanol, isopropanol, hexane, or water, e.g., in a glass scintillation vial. The vial was sealed with a screw cap and heated, e.g., to ~60-80° C., until the material was completely dissolved. The heating temperature could be outside the range of 60-80° C., depending on the composition (e.g., taking into account any added agents that might be heat labile or require higher temperatures to become part of the gel). The vial was placed on a stable surface and allowed to cool to room temperature. Subsequently, an amount of ultrapure water was added and the closed vial was heated again to ~60-80° C., or any other appropriate temperature, until all material was completely dissolved. Gelation occurs after about 15-45 minutes, when no gravitational flow was observed upon inversion of the glass vial. The gel was suspended in ultrapure water and centrifuged for 10 min at 10,000 rpm. The pellet was resuspended in ultrapure water and pulse sonicated at 20 kHz, 30% amplitude, for 2 minutes. This is applicable for most of the formulations, but minor adjustments may be required. Amplitude and time can be varied. Time can be from 30 sec-2 min. Multiple cycles of sonication can be performed.

Results

Particles were developed from ascorbyl palmitate ("AP"), a derivative of vitamin C, and were stabilized using cholesterol. The size of particles and molar ratio of cholesterol to AP is shown in FIGS. 3-6A and 6B. Investigation of the bulk gels formed with scanning electron microscopy (SEM) showed the hydrogels formed fibrous structures with a fiber thickness between tens of nanometers to around 300 nm, and high aspect ratios. Particles derived from bulk gels were observed with cryo-TEM and showed fibrous morphology with diameter between tens of nanometers to around 300 nm, and length of 500-1000 nm. This formulation was evaluated for its encapsulation efficiency of the model hydrophobic drug docetaxel (DTX), which was determined to be 30% by high performance liquid-phase chromatography (HPLC) analysis (FIG. 6C). Particles showed a hydrodynamic diameter of 701.4±15 nm with a polydispersity index (PI) of 0.2-0.4, and a zeta potential of −47.1±4.2 mV. The loading efficiency of docetaxel was determined to be 0.25%. Physiochemical properties of these particles are listed in Table 1.

TABLE 1

| Physiochemical properties of formulation (n = 3) | |
|---|---|
| Parameter | Value |
| Hydrodynamic diameter (nm) | 701.4 ± 15 |
| Polydispersity | 0.3 ± 0.1 |
| Zeta potential (mV) | −47.1 ± 4 |
| Encapsulation efficiency of DTX (%) | 30 ± 1 |
| Loading efficiency of DTX (%) | 0.25 |

Figure 3:
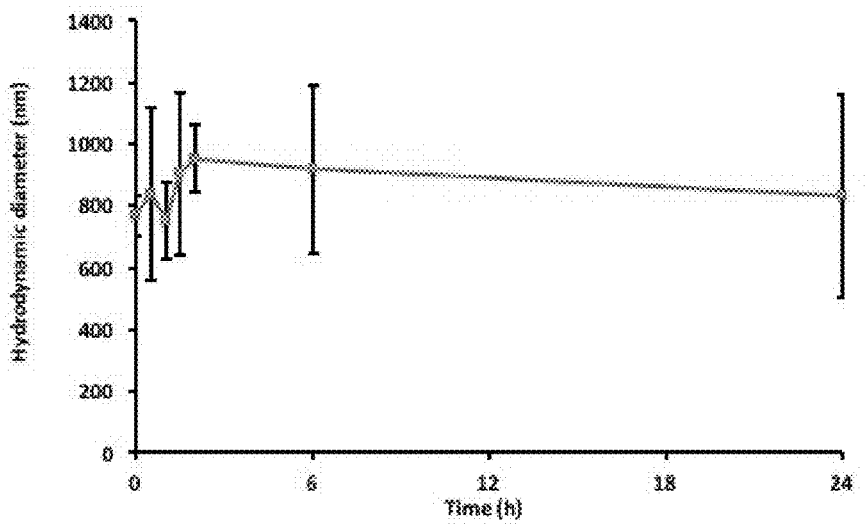
FIG. 3 is a line graph showing the hydrodynamic diameters (nm) of particles over time (hours) after addition into serum.

Serum stability measurements in 10% serum showed stability of particles for at least 24 hours, as indicated by FIG. 3, which shows the hydrodynamic diameter particles did not change significantly in serum over the experimental time frame.

Figure 4:
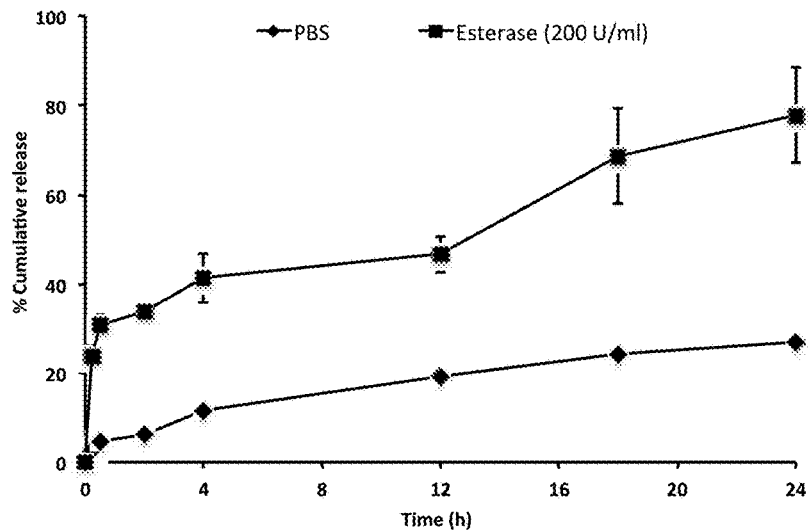
FIG. 4 is a graph of % cumulative release over time (hours) in PBS (diamonds) compared to esterase (200 u/ml) (squares).

FIG. 4 shows the particles had a minimal release (<30%) over 24 hours in phosphate buffered saline (PBS) and a steady release in responsive to esterase (200 U/mL). Esterase is overexpressed in tumors.

Example 2. Different Stabilizing Agents for Particles Against Disassembly in Serum Methods 1 mg/ml suspension of particles was prepared in PBS. 1 ml of particles was added to 1 ml of serum at 37° C. The hydrodynamic diameters of particles in serum was measured at t=0 h, 0.5 h, 1 h, 1.5 h, 2 h and 4 h via dynamic light scattering. Between different time points, particles were incubated at 37° C. Serum alone in dynamic light scattering had a size readout of about 50 nm.

Results

Figure 5A:
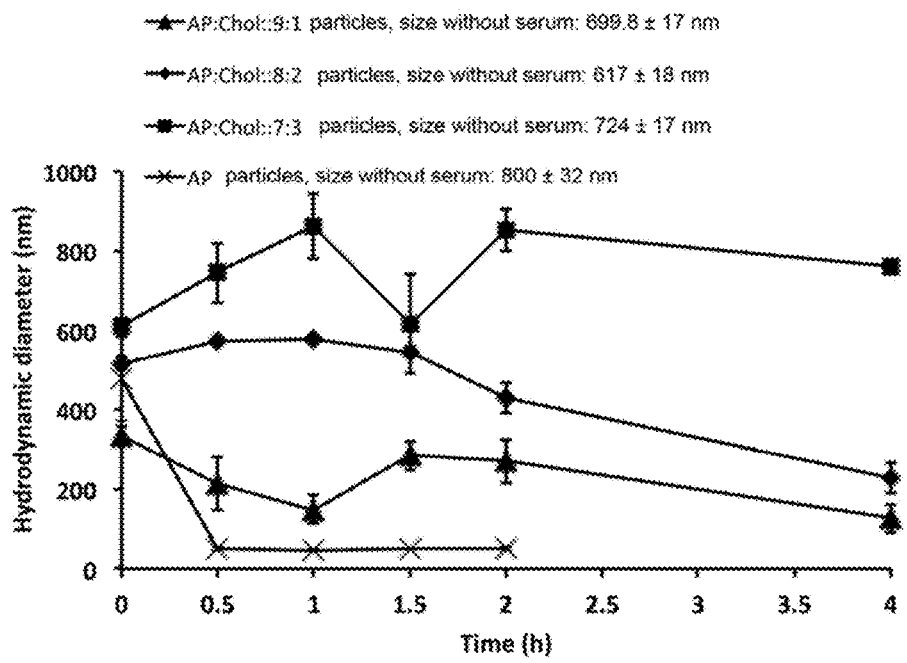
FIG. 5A is a graph of hydrodynamic diameter (nm) over time (hours) after addition of serum for particles assembled with ascorbyl palmitate (AP) and cholesterol (Chol) at a molar ratio 7:3 (squares); AP and Chol at a molar ratio of 8:2 (diamonds); AP and Chol at a molar ratio of 9:1 (triangles); and particles assembled with AP only (x).

FIG. 5A shows the diameter of particles over time in serum, where the particles were made from the assembly of ascorbyl palmitate (AP) in the presence of different amounts of cholesterol. AP particles without cholesterol had a size of 800.8±32 nm before addition into serum, a size of about 500 nm upon addition into serum, and a substantially reduced size of about 50 nm at 0.5 hour after addition to serum and at time points thereafter. The reduced size indicated the instability, i.e. disassembly of previously assembled structures, in serum. Unlike the AP only particles, particles made from the assembly of AP and cholesterol at 9:1 and 8:2 molar ratios had a size of 724.4±16 nm and 617±18 nm, respectively, before addition to serum (FIG. 5A). The presence of cholesterol at 10 mole % and 20 mole % appeared to prevent substantial size reduction for 2 hours in serum. Particles made from the assembly of AP and cholesterol at a 7:3 molar ratio had a size of 699.8±17 nm before addition to serum, and the 30% moles of cholesterol appeared to be required for stabilization of particles in serum for 4 hours.

Figure 5B:
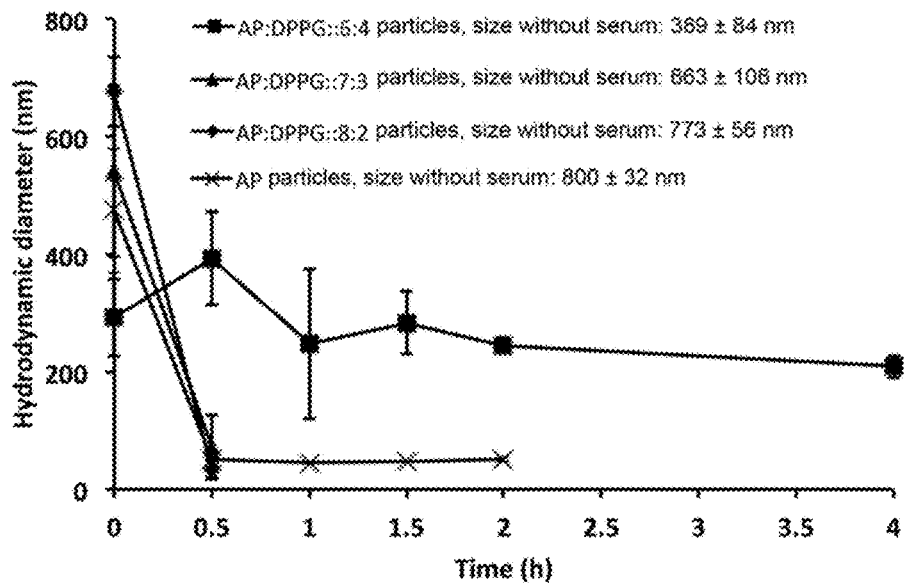
FIG. 5B is a line graph showing the hydrodynamic diameters (nm) of particles over time (hours) after addition of serum: particles assembled with AP and dipalmitoyl phosphatidyl glycerol (DPPG) at a molar ratio of 6:4 (squares); particles assembled with AP and dipalmitoyl phosphatidyl glycerol (DPPG) at a molar ratio of 7:3 (triangle); particles assembled with AP and dipalmitoyl phosphatidyl glycerol (DPPG) at a molar ratio of 8:2 (diamond); and particles assembled with AP (x).

FIG. 5B shows ascorbyl palmitate particles co-assembled with dipalmitoyl phosphatidyl glycerol (DPPG) at a molar ratio of 6:4 for AP:DPPG generally maintained the size in serum for at least 4 hours. These particles had a size of 389±84 nm before addition to serum. This was in contrast to AP particles without DPPG, which substantially decreased in size in as short as 30 minutes in serum.

Figure 5C:
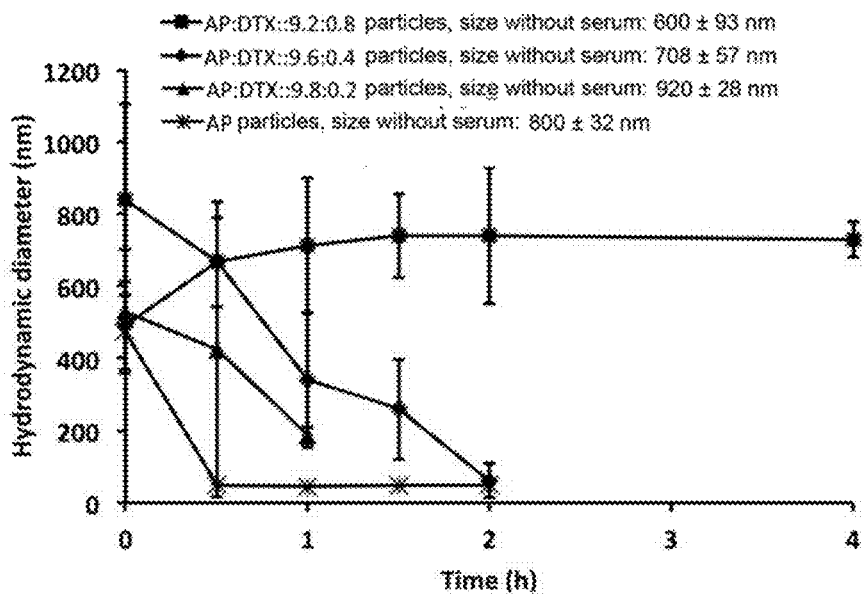
FIG. 5C is a line graph showing the hydrodynamic diameters (nm) of particles over time (hours) after addition into serum: particles assembled with AP and docetaxel (DTX) at a molar ratio of 9.2:0.8 (squares); particles assembled with AP and docetaxel (DTX) at a molar ratio of 9.6:0.4 (diamonds); particles assembled with AP and docetaxel (DTX) at a molar ratio of 9.2:0.8 (squares); and particles assembled with AP (x).

FIG. 5C shows ascorbyl palmitate particles encapsulating docetaxel (DTX) at a molar ratio of 12:1 for AP:DTX generally maintained the size in serum for at least 4 hours. DTX appeared to be a stabilizing agent for the assembled particles. This was in contrast to AP particles without DTX, which substantially decreased in size in as short as 30 minutes in serum.

Example 3. Stabilization of Triglycerol Mono-Sterate Particles by Cholesterol and DPPG Materials and Methods Gels and particles were made as in Example 1. Cholesterol or DPPG were added as stabilizing agents.

Figure 6A:
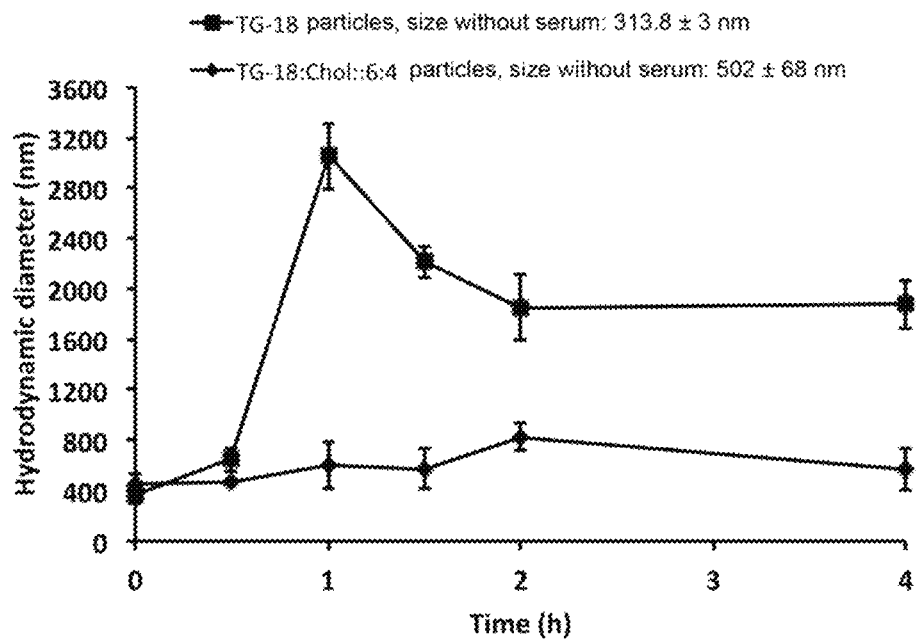
FIGS. 6A and 6B are graphs of hydrodynamic diameter (nm) over time (hours) showing that Cholesterol (Chol) acts as a stabilizing agent for triglycerol mono-stearate (TG-18) particles, and helps prevent their aggregation in 50% serum at 37° C. TG-18 particles, unlike AP particles which tend to aggregate in serum, resulting in an increase in their size over time. This aggregation is prevented by addition of 40 mole % of cholesterol. Size of TG-18 particles in serum at different time points (squares); and size of TG-18:Chol::6:4 particles in serum at different time point (diamonds).

Results FIG. 6A is a graph showing that Cholesterol (Chol) acts as a stabilizing agent for triglycerol monostearate (TG-18) particles, and helps prevent their aggregation in 50% serum at 37° C. TG-18 particles, unlike AP particles which tend to aggregate in serum, resulting in an increase in their size over time. This aggregation is prevented by addition of 40 mole % of cholesterol.

Figure 6B:
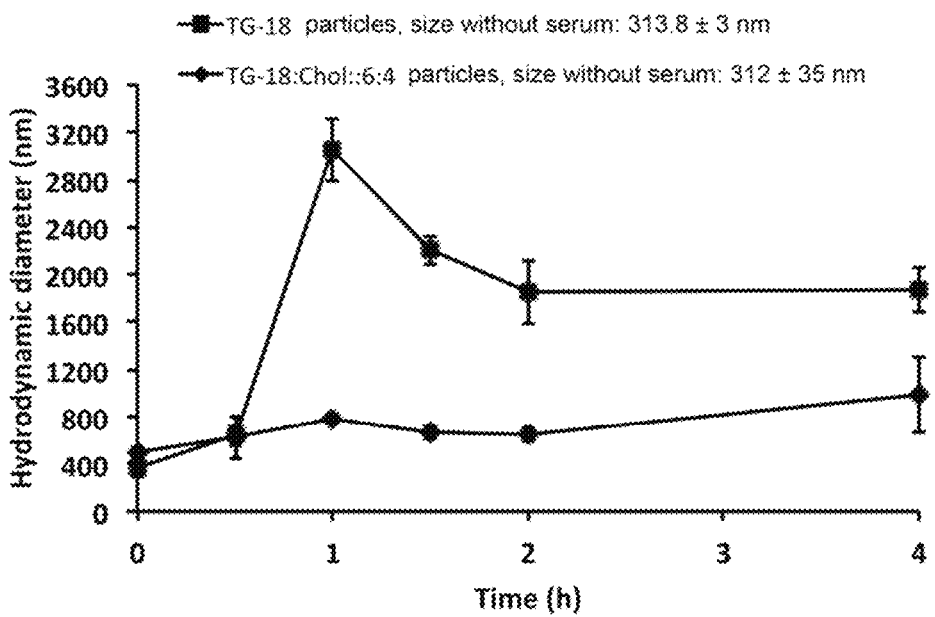
Figure 6C:
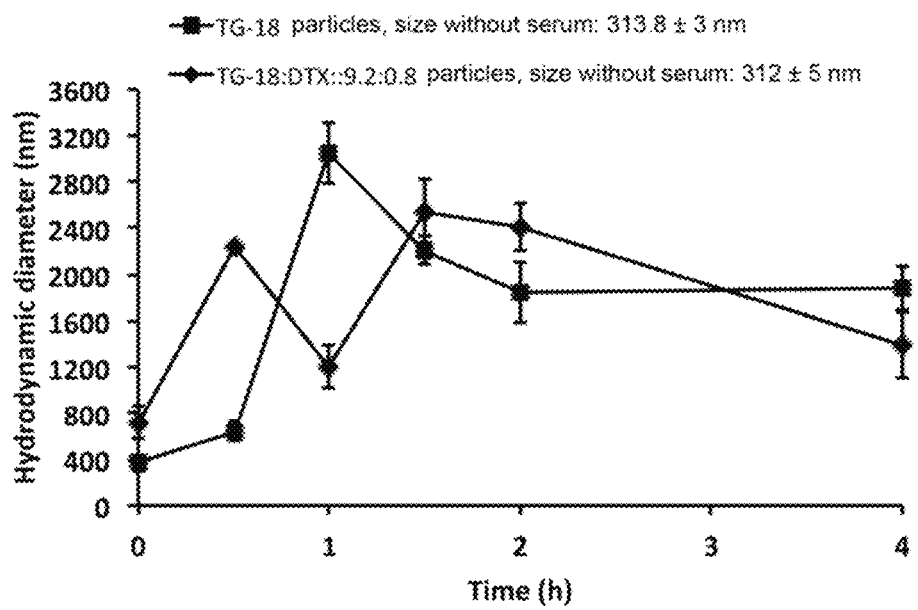
FIG. 6C is a graph showing that Docetaxel (DTX) does not stabilize triglycerol mono-stearate (TG-18) particles, and do not help in preventing their aggregation in 50% serum at 37° C. TG-18 particles, unlike AP particles tend to aggregate in serum, resulting in an increase in their size over time. This aggregation is not prevented by addition of 8 mole % of DTX. Size of TG-18 particles in serum at different time points (squares); and size of TG-18:DTX::9.2:0.8 particles in serum at different time points (diamonds).

FIG. 6B is a graph showing that DPPG acts as a stabilizing agent for triglycerol mono-stearate (TG-18) particles, and helps in preventing their aggregation in 50% serum at 37° C. TG-18 particles, unlike AP particles tend to aggregate in serum, resulting in an increase in their size over time. This aggregation is prevented by addition of 40 mole % of DPPG.

FIG. 6C is a graph showing that Docetaxel (DTX) does not stabilize triglycerol mono-stearate (TG-18) particles, and do not help in preventing their aggregation in 50% serum at 37° C. TG-18 particles, unlike AP particles tend to aggregate in serum, resulting in an increase in their size over time. This aggregation is not prevented by addition of 8 mole % of DTX.

Example 4. Stabilization of Sorbiton Mono-Sterate Particles by Cholesterol and DPPG Materials and Methods Gels and particles were made as in Example 1. Cholesterol or DPPG were added as stabilizing agents.

Results

Figure 7A:
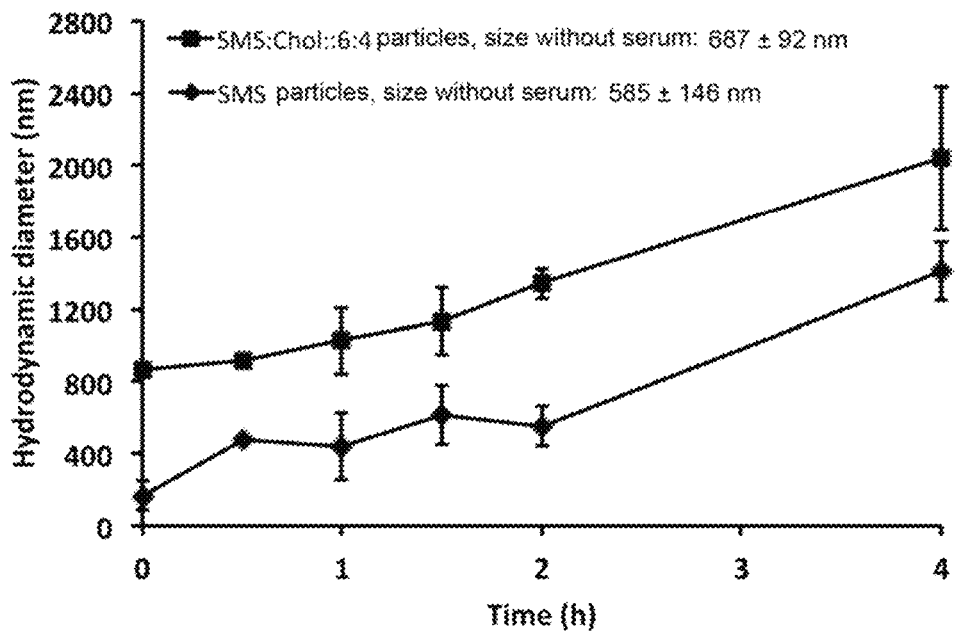
FIG. 7A is a graph of hydrodynamic diameter (nm) over time (hours) showing Cholesterol (Chol) partially stabilizes sorbiton mono-stearate (SMS) particles in 50% serum at 37° C. SMS particles tend to show immediate disassembly in serum, resulting in a drastic and rapid reduction in their size, and this is followed by their aggregation, resulting in an increase in their size over time. Size of SMS particles in serum at different points (diamond). At time t=0, the size of SMS particles drops from 585 nm (size in PBS) to 160 nm, indicating their disassembly in serum. Subsequently, the size increases due to aggregation. Size of SMS:Chol::6:4 particles is shown by squares. Results indicate that addition of 40 mole % of chol prevents initial disassembly but do not prevent subsequent aggregation.

FIG. 7A is a graph showing Cholesterol (Chol) partially stabilizes sorbiton mono-stearate (SMS) particles in 50% serum at 37° C. SMS particles tend to show immediate disassembly in serum, resulting in a drastic and rapid reduction in their size, and this is followed by their aggregation, resulting in an increase in their size over time. At time t=0, the size of SMS particles drops from 585 nm (size in PBS) to 160 nm, indicating their disassembly in serum. Subsequently, the size increases due to aggregation. Addition of 40 mole % of chol prevents initial disassembly but do not prevent subsequent aggregation.

Figure 7B:
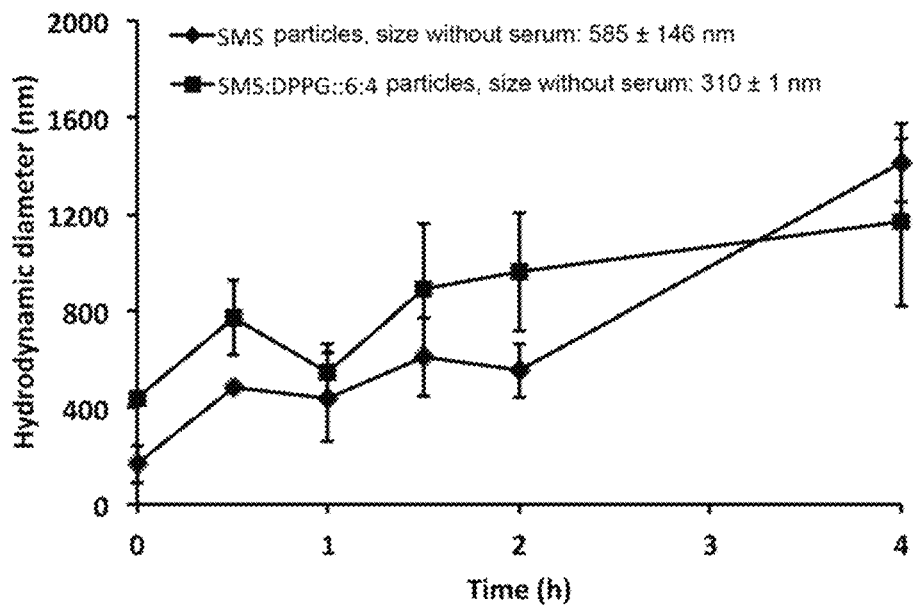
FIG. 7B is a graph showing DPPG partially stabilizes sorbiton mono-stearate (SMS) particles in 50% serum at 37° C. SMS particles tend to show immediate disassembly in serum, resulting in a drastic and rapid reduction in their size, and this is followed by their aggregation, resulting in an increase in their size over time. Size of SMS particles in serum at different points (diamond). At time t=0, the size of SMS particles drops from 585 nm (size in PBS) to 160 nm, indicating their disassembly in serum. Subsequently, the size increases due to aggregation. Size of SMS:DPG::6:4 particles (squares). Results indicate that addition of 40 mole % of DPPG prevents initial disassembly but do not prevent subsequent aggregation.

FIG. 7B is a graph showing DPPG partially stabilizes sorbiton mono-stearate (SMS) particles in 50% serum at 37° C. SMS particles tend to show immediate disassembly in serum, resulting in a drastic and rapid reduction in their size, and this is followed by their aggregation, resulting in an increase in their size over time. At time t=0, the size of SMS particles drops from 585 nm (size in PBS) to 160 nm, indicating their disassembly in serum. Subsequently, the size increases due to aggregation. Addition of 40 mole % of DPPG prevents initial disassembly but do not prevent subsequent aggregation.

Example 5. Inhibition on Cancer Cell Metabolism In Vitro, Synergistic Efficacy in Delivery Chemotherapeutics, and Partition in Tumor Tissues In Vivo Materials and Methods Particles were made in the same method as shown in Example 1.

Nanofiber cytotoxicity was studied in vitro in prostate cancer cells—PC3 and LNCaP.

In vivo biodistribution study of particles was performed in Balb/c mice using a subcutaneous 4T3 murine breast cancer model. Mice were divided into three groups, with three mice per group—a control group with no treatment, a test group of ascorbyl palmitate particles loaded with a dye (DiR), and another test group of free dye.

Results

Figure 8A:
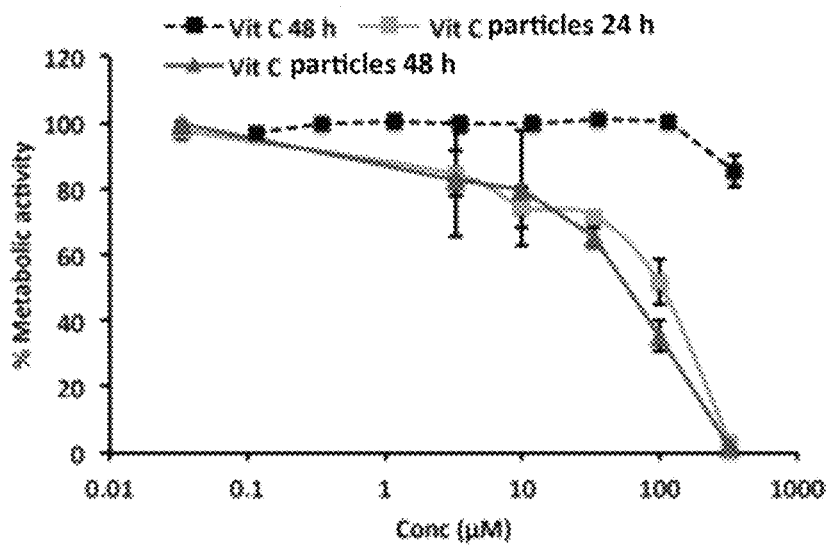
FIG. 8A is a line graph showing the % metabolic activity of PC3 (PC-3) human prostate cancer cells incubated with a range of concentrations (μM) of a vitamin C solution for 48 hours ("Vit C 48 h", black square) or of stabilized vitamin C-derived particles for 24 hours or 48 hours ("Vit C particles 24 h" (grey square) and "Vit C particles 48 h" (triangle), respectively).
Figure 8B:
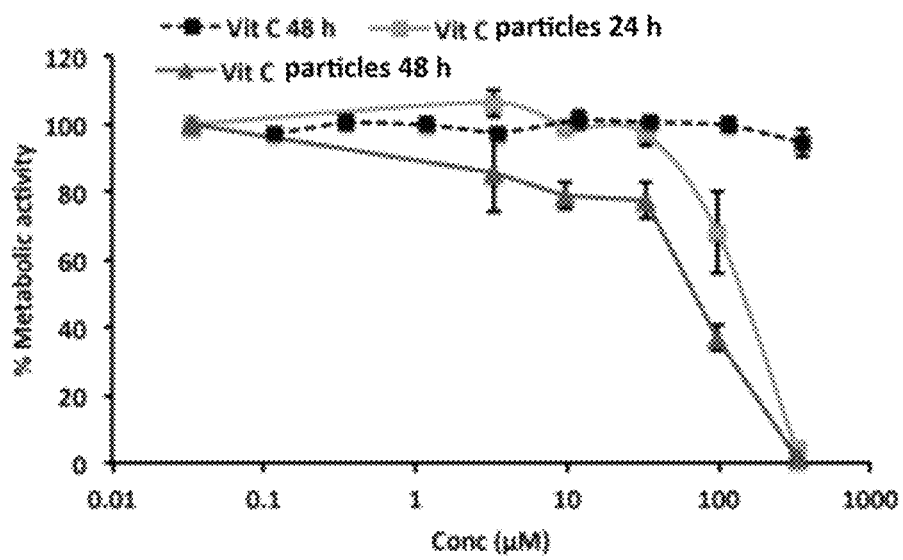
FIG. 8B is a line graph showing the % metabolic activity of LNCaP androgen-sensitive human prostate adenocarcinoma cells incubated with Vit C for 48 hours (black squares), Vit C particles for 24 hours (grey squares), and Vit C particles for 48 hours (triangles).

FIG. 8A is a line graph showing the % metabolic activity of PC3 (PC-3) human prostate cancer cells incubated with a range of concentrations ($\Xi$M) of a vitamin C solution for 48 hours ("Vit C 48 h", black square) or of stabilized vitamin C-derived particles for 24 hours or 48 hours ("Vit C particles 24 h" (grey square) and "Vit C particles 48 h" (triangle), respectively). FIG. 8B is a line graph showing the % metabolic activity of LNCaP androgen-sensitive human prostate adenocarcinoma cells incubated with Vit C for 48 hours (black squares), Vit C particles for 24 hours (grey squares), and Vit C particles for 48 hours (triangles).

Figure 9A:
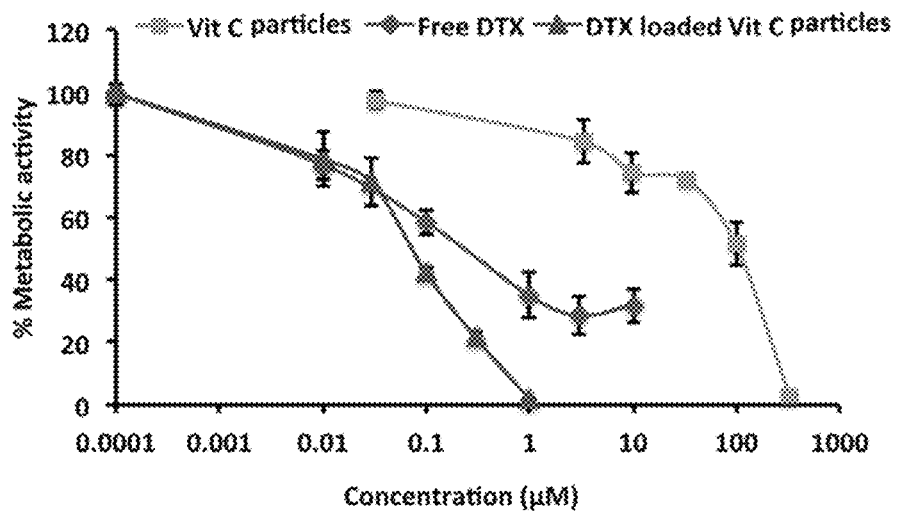
FIGS. 9A and 9B are line graphs showing the % metabolic activity of PC3 cells (FIG. 9A) and the % metabolic activity of LNCaP cells (FIG. 9B) when incubated with a range of concentrations (μM) of stabilized vitamin C-derived particles ("Vit C particles", grey squares), of free docetaxel ("free DTX", diamonds), or of stabilized vitamin C-derived particles encapsulating docetaxel ("DTX loaded Vit C particles", triangles).
Figure 9B:
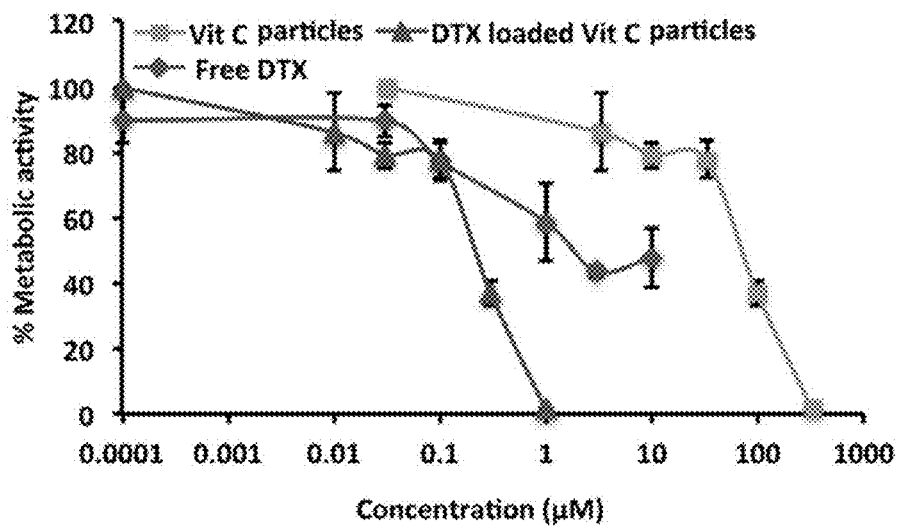

FIGS. 9A and 9B are line graphs showing the % metabolic activity of PC3 cells (FIG. 9A) and the % metabolic activity of LNCaP cells (FIG. 9B) when incubated with a range of concentrations (μM) of stabilized vitamin C-derived particles ("Vit C particles", grey squares), of free docetaxel ("free DTX", diamonds), or of stabilized vitamin C-derived particles encapsulating docetaxel ("DTX loaded Vit C particles", triangles).

Using ascorbyl palmitate as the gelator, particles releasing ascorbic acid, i.e., vitamin C, showed an improved anticancer efficacy compared to vitamin C solution. The half maximal inhibitory concentration ($IC_{50}$) of vitamin C particles for prostate cancer cells was found to be in the range between 40 and 60 μM. However, vitamin C solution did not show any effect at this concentration. This could have implications toward reducing the therapeutic dosage of vitamin C for cancer patients.

Ascorbyl palmitate particles loaded with a chemotherapeutic agent, docetaxel (DTX), exhibited an enhanced anti-cancer effect between DTX and vitamin C, in inhibiting or killing prostate cancer cells. $IC_{50}$ values of these particles were determined to be 0.07 µM and 0.13 µM for PC-3 cells and LNCaP cells, respectively; which were much less than the $IC_{50}$ of free DTX which was 0.62 µM and 3.6 µM for PC-3 cells and LNCaP cells, respectively. This indicated the particles significantly increased the effectiveness of the encapsulated drug by lowering the concentration necessary for half maximal inhibition. Table 2 shows the combination indices based on Chou Talaly's Combination Index were less than one, indicating synergism between the vitamin C and the encapsulated chemotherapeutic.

TABLE 2

$IC_{50}$ (µM) and combination index for formulation in cancer cell lines (n = 3)

| Formulation | PC3 | LNCaP |
| --- | --- | --- |
| Free DTX | 0.62 | 3.6 |
| Vitamin C NF | 48.3 | 61.8 |
| DTX loaded Vitamin C NF | 0.07 | 0.13 |
| Chou Talaly's Combination Index | 0.57 | 0.71 |

It was believed therapeutic efficacy would be enhanced when the encapsulated agents were combined with other agents such as vitamin K or its prodrugs entrapped, co-assembled, or as a gelator.

Figure 10:
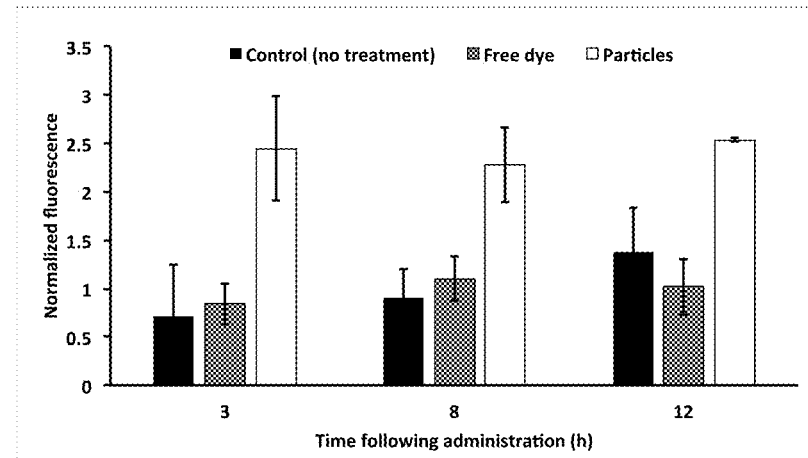
FIG. 10 is a bar graph showing the normalized fluorescence of a dye (DiR) in mouse tumor tissues over time (hour) for control (no treatment) mice, and for mice administered with free dye or with stabilized vitamin C-derived particles encapsulating the dye at 3, 8, and 12 hours following administration.

FIG. 10 is a bar graph showing the normalized fluorescence of a dye (DiR) in mouse tumor tissues over time (hour) for control (no treatment) mice, and for mice administered with free dye or with stabilized vitamin C-derived particles encapsulating the dye at 3, 8, and 12 hours following administration. FIG. 10 shows particles had an increased accumulation in tumor tissue as compared to control (no injection) and injection with free dye, as quantified from fluorescent imaging of the tumor tissues at different hours following administration.

Figure 11A:
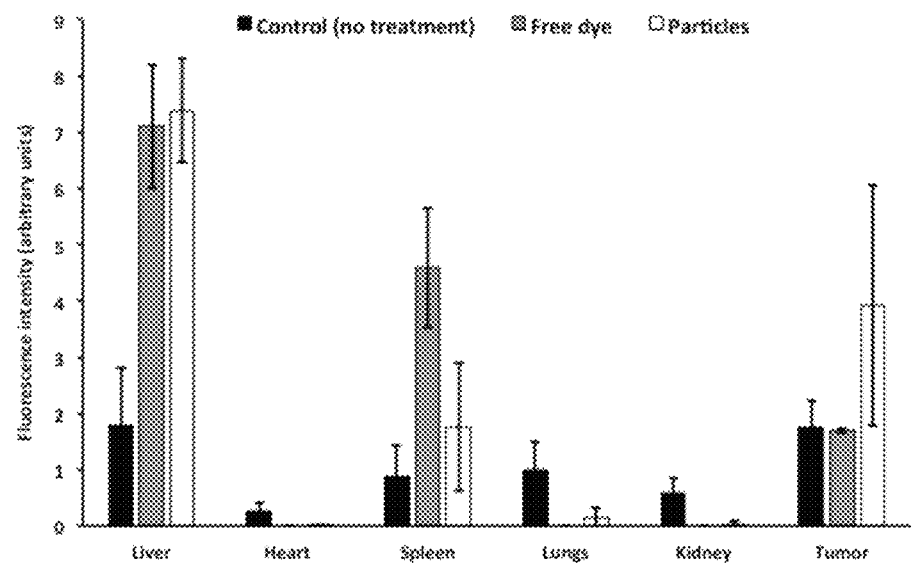
FIGS. 11A and 11B are bar graphs showing the tissue distribution of an administered dye in its free form or loaded in stabilized vitamin C-derived particles in mice with a breast cancer.
Figure 11B:
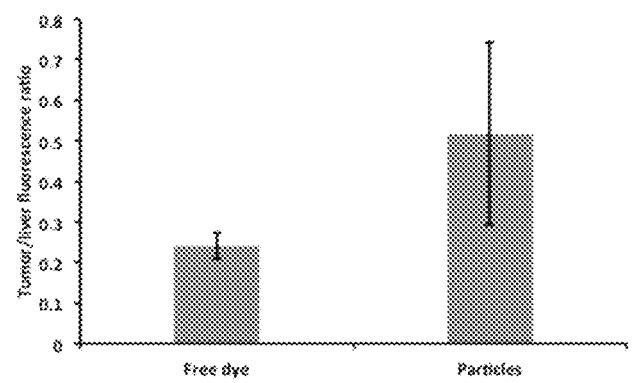

FIGS. 11A and 11B are bar graphs showing the tissue distribution of an administered dye in its free form or loaded in stabilized vitamin C-derived particles in mice with a breast cancer. FIG. 11A shows the fluorescence intensity of the dye in different tissues. FIG. 11B shows the ratio of fluorescence in tumor to fluorescence in liver. FIGS. 11A and 11B show the ratio of accumulation in tumor to liver was significantly higher for particles than for free dye.

We claim:

1. A self-assembled organo or hydrogel composition comprising
one or more low molecular weight amphiphilic gelators having a molecular weight of less than 2,500 Da and
one or more aggregation decreasing agents selected from the group consisting of sterols, phospholipids, and a combination thereof,
wherein the gelators and the aggregation decreasing agents co-assemble into hydrogel or organo-gel comprising nanostructures,
wherein the aggregation decreasing agent is at least 15 mole % of the composition.

2. The composition of claim 1 wherein the gelator is a compound meeting the requirements of the U.S. Food and Drug Administration as a generally recognized as safe (GRAS) compound.

3. The composition of claim 1, wherein the gelator is selected from the group consisting of ascorbyl alkanoate, sorbitan alkanoate, triglycerol monoalkanoate, sucrose alkanoate, glycocholic acid, and combinations thereof.

4. The composition of claim 3, wherein the gelator is ascorbyl palmitate.

5. The composition of claim 1 wherein the aggregation decreasing agent imparts rigidity, increases the packing density, and/or enhances the strength of assembled structures, thus altering the phase transition process and transitioning temperature, and/or modulating the surface properties of bulk gel or particles thereof to reduce or prevent protein adhesion or accumulation.

6. The composition of claim 1, wherein the aggregation decreasing agent is at least 20, 25, or 30 mole % of the composition.

7. The composition of claim 1, wherein the aggregation decreasing agent is cholesterol.

8. The composition of claim 1, wherein the aggregation decreasing agent is a phospholipid.

9. The composition of claim 1, wherein the aggregation decreasing agent is dipalmitoyl phosphatidyl glycerol.

10. The composition of claim 1, wherein the nanostructures comprise fibers, lamellar structures, micellar structures, vesicular structures, sheets or tape-like structures.

11. The composition of claim 1, wherein the hydrogel or organo-gel are in the form of particles.

12. The composition of claim 1, wherein the nanostructures have a hydrodynamic diameter between 300 nm and 900 nm.

13. The composition of claim 1, further comprising one or more therapeutic, prophylactic, or diagnostic agents.

14. The composition of claim 1 further comprising one or more pharmaceutical excipients.

15. The composition of claim 1 comprising a kit comprising a dosage unit.

16. The kit of claim 15, wherein the dosage unit comprises one or more containers for dry components and one or more containers for liquid components, which mixed together form the self-assembled composition.

17. A method of preparing a serum-stabilized, self-assembled hydro- or organo-gel composition comprising nanostructures, comprising:
Combining one or more low molecular weight amphiphilic gelators of less than 2,500 Da, one or more aggregation decreasing agents as defined by claim 1, and optionally a therapeutic, prophylactic, or diagnostic agents to form an organo or hydrogel comprising nanostructures.

18. The method of claim 17 wherein the nanostructures are formed from the gelator and incorporate the aggregation decreasing agent.

19. The method of claim 17 wherein the nanostructures are formed and then the aggregation decreasing agent is added to the nanostructures.

20. The method of claim 17 comprising adding to the organo or hydrogel a therapeutic, prophylactic or diagnostic agent.

21. The method of claim 17 further comprising physically separating the organo or hydrogel into particles.

22. The method of claim 17 comprising adding one or more gelators in a polar solvent by mixing or heating,
allowing the mixture to cool,
dissolving the mixture in water by mixing or heating, where gelation occurs,
and optionally removing un-assembled agents and un-encapsulated agents by centrifugation.

23. A method of isolating particles with or without aggregation decreasing agents from the organo or hydrogel of claim 1, comprising:
adding water or a solvent or a solution to the organo or hydro gel,
mixing rapidly,
centrifuging, and
removing the supernatant to separate particles of the organo or hydrogel from the organo or hydrogel of claim 1.

24. The method of claim 23 comprising adding an aqueous solution or solvent to the centrifuged particles, and dispersing the particles in the aqueous solution by mixing with or without pulse sonication for 2 min.

25. A method of delivering a therapeutic, prophylactic, or diagnostic agent to a subject, comprising administering the composition of claim 13.

26. The method of claim 25, wherein the composition is administered intravenously.

27. The method of claim 25, wherein the composition accumulates in tumors compared to an agent delivered in its free form or in a self-assembled hydrogel or organo-gel without a aggregation decreasing agent.

28. The composition of claim 1, wherein the composition lacking the one or more aggregation decreasing agents aggregates to at least about twice the size the composition lacking the stabilizing agents was prior to exposure to serum proteins for at least 30 minutes in the presence of serum proteins in phosphate buffered saline at 37° C.

29. The composition of claim 28, wherein the gelator is a triglycerol monoalkanoate.

30. The composition of claim 28, wherein the gelator is triglycerol mono-stearate.

* * * * *